(12) United States Patent
Shraga

(10) Patent No.: US 7,621,931 B2
(45) Date of Patent: Nov. 24, 2009

(54) ADJUSTABLE LANCET DEVICE AND METHOD

(75) Inventor: Steven Shraga, Surfside, FL (US)

(73) Assignee: Stat Medical Devices, Inc., North Miami Beach, FL (US)

( * ) Notice: Subject to any disclaimer, the term of this patent is extended or adjusted under 35 U.S.C. 154(b) by 1131 days.

(21) Appl. No.: 10/441,065

(22) Filed: May 20, 2003

(65) Prior Publication Data
US 2004/0236362 A1    Nov. 25, 2004

(51) Int. Cl.
*A61B 17/32* (2006.01)
(52) U.S. Cl. ........................ 606/182; 606/181
(58) Field of Classification Search ................. 606/182, 606/181
See application file for complete search history.

(56) References Cited

U.S. PATENT DOCUMENTS

| | | |
|---|---|---|
| 676,678 A | 6/1901 | Ellifrits |
| 1,135,465 A | 4/1915 | Pollock |
| 2,848,809 A | 8/1958 | Crowder |
| 3,589,213 A | 6/1971 | Gourley |
| 4,139,011 A | 2/1979 | Benoit et al. |
| 4,203,446 A | 5/1980 | Höfert et al. |
| 4,257,561 A | 3/1981 | McKinney |
| 4,388,925 A | 6/1983 | Burns |
| 4,426,105 A | 1/1984 | Plaquin et al. |
| 4,449,529 A | 5/1984 | Burns et al. |
| 4,469,110 A | 9/1984 | Slama |
| 4,517,978 A | 5/1985 | Levin et al. |
| 4,527,561 A | 7/1985 | Burns |
| 4,628,929 A | 12/1986 | Intengan et al. |
| 4,785,858 A | 11/1988 | Valentini et al. |
| RE32,922 E | 5/1989 | Levin et al. |
| 4,834,667 A | 5/1989 | Fowler et al. |
| 4,858,607 A | 8/1989 | Jordan et al. |
| 4,869,249 A | 9/1989 | Crossman et al. |
| 4,895,147 A | 1/1990 | Bodicky et al. |
| 4,924,879 A | 5/1990 | O'Brien |

(Continued)

FOREIGN PATENT DOCUMENTS

CA        523078        3/1956

(Continued)

OTHER PUBLICATIONS

Sutor et al., "Bleeding from Standardized Skin Punctures: Automated Technic for Recording Time, Intensity, and Pattern of Bleeding", A.J.C.P., vol. 55, pp. 541-546 (May 1971).

*Primary Examiner*—Corrine M McDermott
*Assistant Examiner*—Christopher D Prone
(74) *Attorney, Agent, or Firm*—Greenblum & Bernstein, P.L.C.

(57) ABSTRACT

Lancet device that includes a body. A trigger is mounted to the body. A front cover has a skin engaging end that includes a lancet opening through which a lancet needle extends. A holding member is movably mounted within the body and includes a front end a rear end. The front end can be configured to receive a lancet. A stop surface moves with the holding member. A cam disk includes cam surfaces which can be contacted by the stop surface. The cam disk is configured to rotate at least partially. The cam disk rotates about an axis that is not parallel to an axis running through at least one of the lancet opening and the holding member.

74 Claims, 16 Drawing Sheets

U.S. PATENT DOCUMENTS

| | | | |
|---|---|---|---|
| 4,976,724 A | 12/1990 | Nieto et al. | |
| 4,990,154 A | 2/1991 | Brown et al. | |
| 5,074,872 A | 12/1991 | Brown et al. | |
| 5,147,375 A | 9/1992 | Sullivan et al. | |
| 5,196,025 A * | 3/1993 | Ranalletta et al. | 606/182 |
| 5,212,879 A | 5/1993 | Biro et al. | |
| 5,269,799 A | 12/1993 | Daniel | |
| 5,282,822 A | 2/1994 | Macors et al. | |
| 5,304,193 A * | 4/1994 | Zhadanov | 606/182 |
| 5,318,584 A | 6/1994 | Lange et al. | |
| 5,324,303 A | 6/1994 | Strong et al. | |
| 5,350,392 A | 9/1994 | Purcell et al. | |
| 5,356,420 A | 10/1994 | Czernecki et al. | |
| 5,366,470 A | 11/1994 | Ramel | |
| 5,395,388 A | 3/1995 | Schraga | |
| 5,423,847 A | 6/1995 | Strong et al. | |
| 5,439,473 A | 8/1995 | Jorgensen | |
| 5,454,828 A | 10/1995 | Schraga | |
| 5,464,418 A | 11/1995 | Schraga | |
| 5,476,101 A | 12/1995 | Schramm et al. | |
| 5,509,345 A | 4/1996 | Cyktich | |
| 5,518,004 A | 5/1996 | Schraga | |
| 5,554,166 A * | 9/1996 | Lange et al. | 606/182 |
| 5,569,286 A | 10/1996 | Peckham et al. | |
| 5,569,287 A | 10/1996 | Tezuka et al. | |
| D376,203 S | 12/1996 | Schraga | |
| 5,613,978 A * | 3/1997 | Harding | 606/181 |
| 5,628,764 A | 5/1997 | Schraga | |
| 5,628,765 A | 5/1997 | Morita | |
| 5,643,306 A | 7/1997 | Schraga | |
| 5,730,753 A * | 3/1998 | Morita | 606/181 |
| 5,741,288 A | 4/1998 | Rife | |
| RE35,803 E | 5/1998 | Lange et al. | |
| 5,797,942 A | 8/1998 | Schraga | |
| 5,873,887 A | 2/1999 | King et al. | |
| 5,879,367 A | 3/1999 | Latterell et al. | |
| 5,908,434 A | 6/1999 | Schraga | |
| 5,916,230 A | 6/1999 | Brenneman et al. | |
| 5,984,940 A | 11/1999 | Davis et al. | |
| 6,022,366 A | 2/2000 | Schraga | |
| 6,045,567 A | 4/2000 | Taylor et al. | |
| 6,056,765 A | 5/2000 | Bajaj et al. | |
| 6,071,294 A | 6/2000 | Simons et al. | |
| D428,150 S | 7/2000 | Ruf et al. | |
| 6,136,013 A | 10/2000 | Marshall et al. | |
| 6,152,942 A | 11/2000 | Brenneman et al. | |
| 6,156,050 A | 12/2000 | Davis et al. | |
| 6,156,051 A | 12/2000 | Schraga | |
| 6,168,606 B1 | 1/2001 | Levin et al. | |
| 6,183,489 B1 | 2/2001 | Douglas et al. | |
| 6,190,398 B1 | 2/2001 | Schraga | |
| 6,192,891 B1 | 2/2001 | Gravel et al. | |
| 6,197,040 B1 | 3/2001 | Le Vaughn et al. | |
| 6,210,420 B1 | 4/2001 | Mauze | |
| 6,221,089 B1 | 4/2001 | Mawhirt | |
| 6,228,100 B1 | 5/2001 | Schraga | |
| 6,258,112 B1 | 7/2001 | Schraga | |
| 6,283,982 B1 | 9/2001 | Levaughn et al. | |
| 6,306,152 B1 | 10/2001 | Verdonk et al. | |
| 6,322,574 B1 | 11/2001 | Lloyd et al. | |
| 6,322,575 B1 | 11/2001 | Schraga | |
| 6,332,871 B1 | 12/2001 | Douglas et al. | |
| 6,346,114 B1 | 2/2002 | Schraga | |
| 6,364,889 B1 | 4/2002 | Kheiri et al. | |
| 6,379,317 B1 | 4/2002 | Kintzig et al. | |
| 6,409,740 B1 | 6/2002 | Kuhr et al. | |
| 6,419,661 B1 | 7/2002 | Kuhr et al. | |
| 6,451,040 B1 | 9/2002 | Purcell | |
| 6,464,649 B1 | 10/2002 | Duchon et al. | |
| 6,506,168 B1 | 1/2003 | Fathallah et al. | |
| 6,514,270 B1 | 2/2003 | Schraga | |
| 6,540,762 B1 | 4/2003 | Bertling | |
| 6,558,402 B1 * | 5/2003 | Chelak et al. | 606/182 |
| 6,887,253 B2 | 5/2005 | Schraga | |
| 6,958,072 B2 | 10/2005 | Schraga | |
| 2003/0028126 A1 * | 2/2003 | List | 600/583 |
| 2003/0187470 A1 * | 10/2003 | Chelak et al. | 606/182 |

FOREIGN PATENT DOCUMENTS

| | | |
|---|---|---|
| EP | 0061102 | 9/1982 |
| EP | 0137975 | 4/1985 |
| EP | 0189117 | 7/1986 |
| EP | 0885590 | 12/1998 |
| EP | 0904731 | 3/1999 |
| EP | 1074219 | 2/2001 |
| FR | 1126718 | 11/1956 |

* cited by examiner

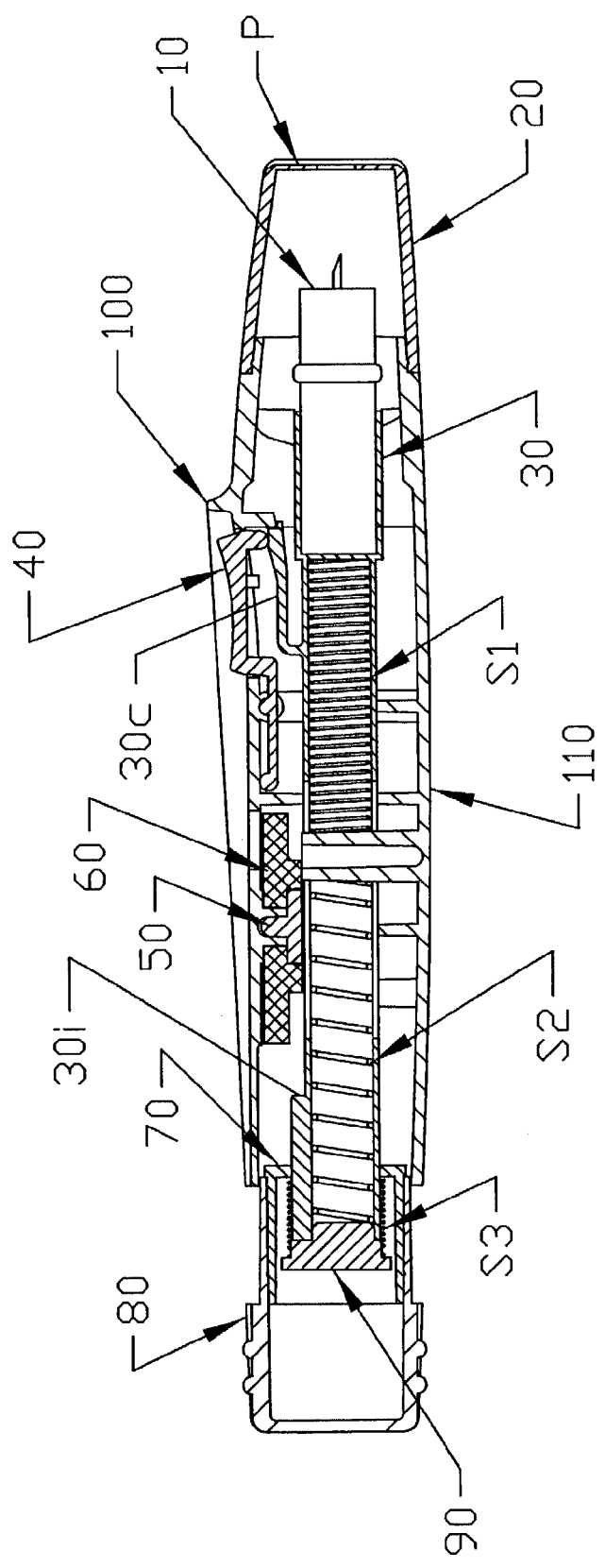

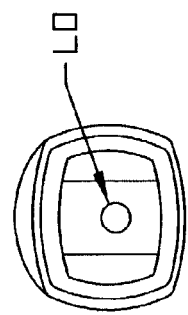
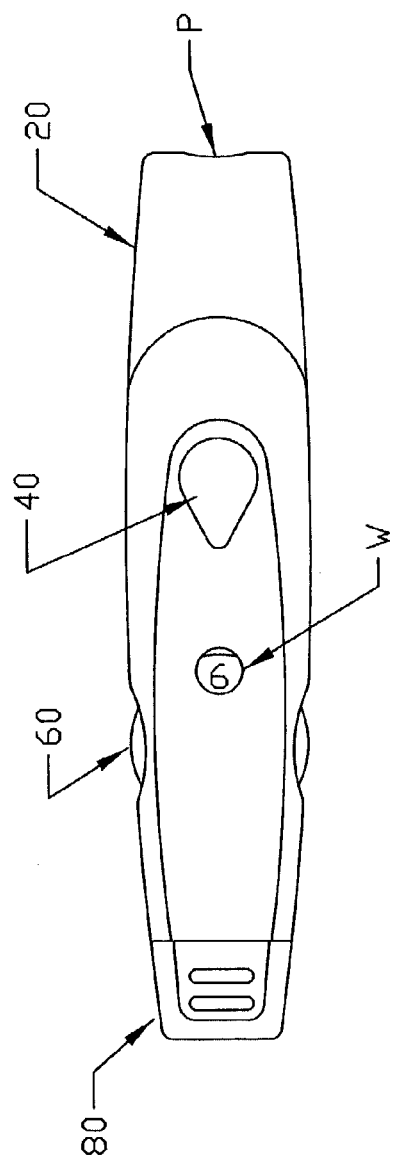
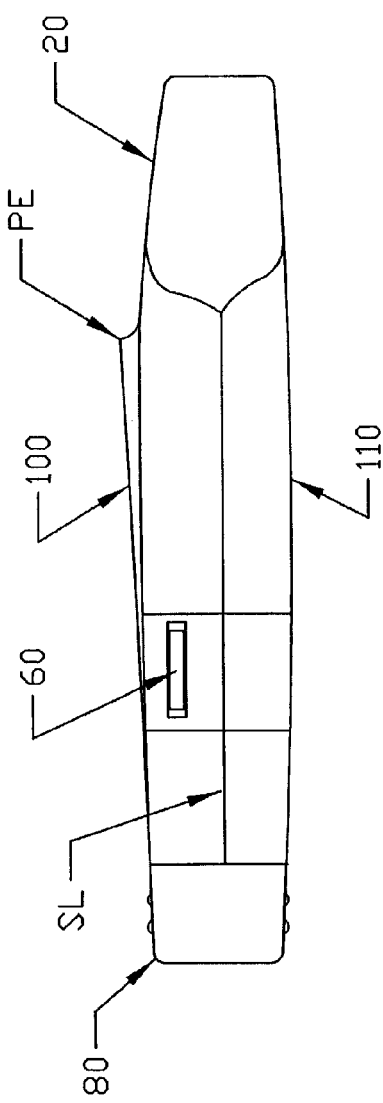

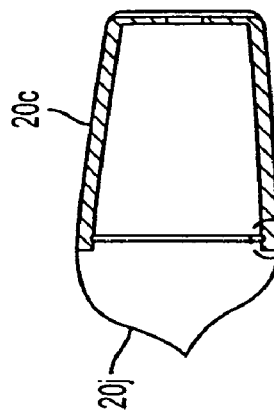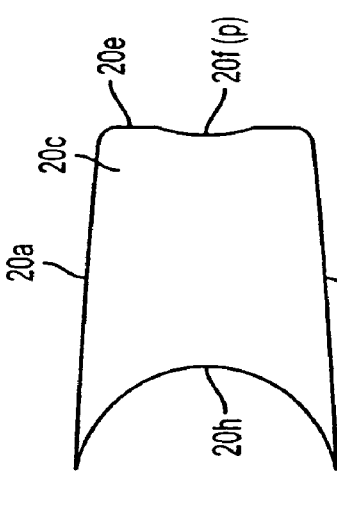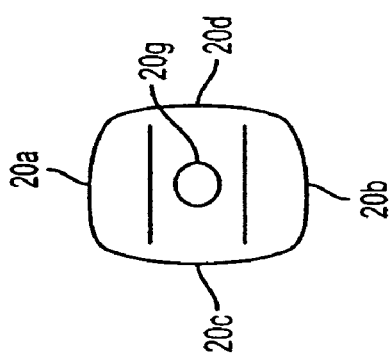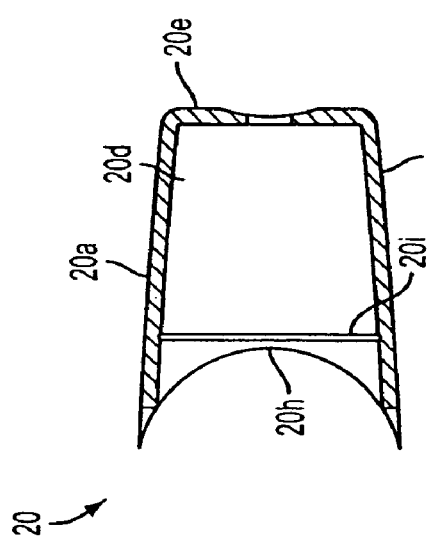
FIG. 9C
FIG. 9F
FIG. 9B
FIG. 9E
FIG. 9A
FIG. 9D

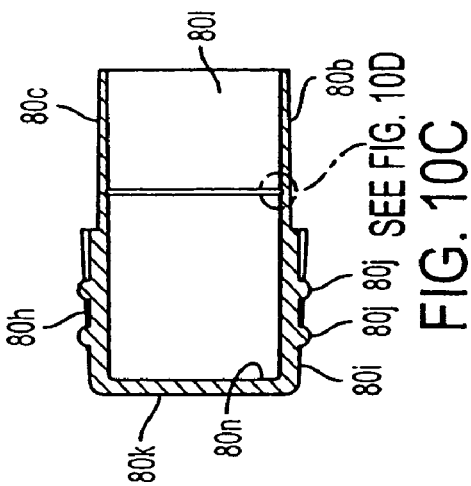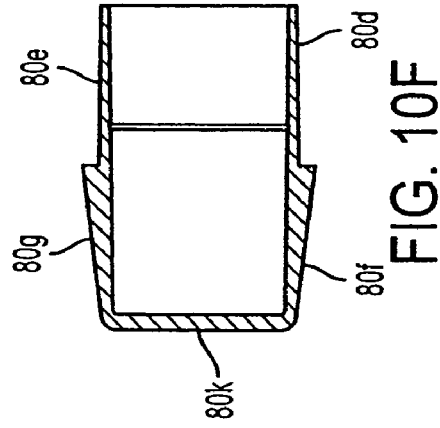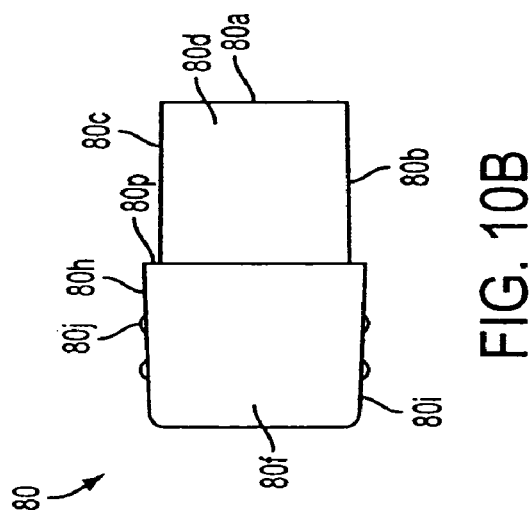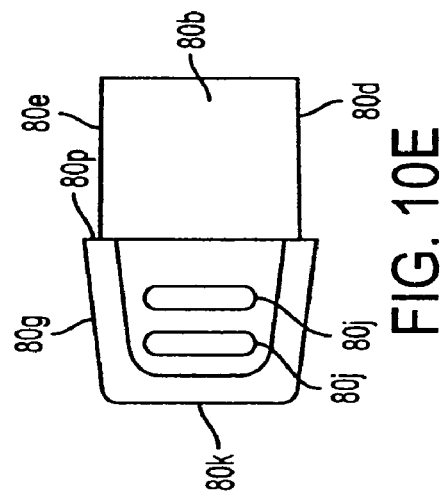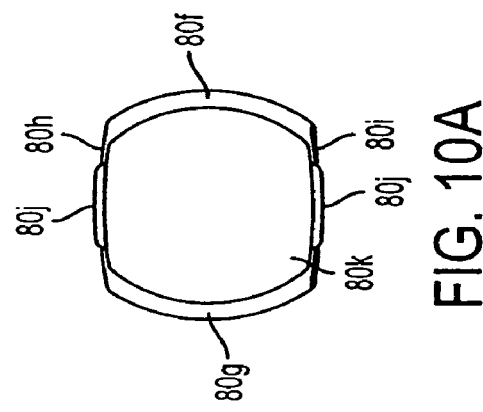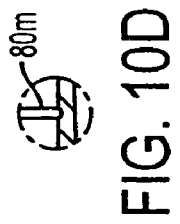

ADJUSTABLE LANCET DEVICE AND METHOD

BACKGROUND OF THE INVENTION

1. Field of the Invention

The invention relates to a lancet device having an adjusting capability, and a method of using a lancet device. In particular, the invention relates to a lancet device which utilizes an adjustable depth penetration. Lancet devices are used to penetrate and puncture the skin in order to allow the taking of a blood sample for testing. The present device allows the user to control the depth of this penetration by a simple adjustment mechanism.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Moreover, controlling the depth of penetration cannot be reliably accomplished without the use of a mechanical device. Additionally, many users simply cannot perform the procedure owing to either a fear of needles or because they lack a steady hand. As a result, lancet devices have been developed which allow the user to more easily and reliably perform this procedure.

Most lancet devices lack convenient and flexible adjustability. Such devices are typically made adjustable by switching their tips. U.S. Pat. No. Re. 32,922 to LEVIN et al. is one such device. That is, the user must remove one tip having a set depth and replace it with another having a different set depth. This, of course, creates the problem of storing the replaceable tips, which if not properly done, may result in their misplacement, damage, contamination, or the like.

An improved device would allow the user to more easily adjust the depth of penetration and would overcome some of the disadvantages described above. Moreover, since the skin thickness can vary slightly from user to user and finger to finger, a need exists for efficiently adapting the depth of penetration. For example, an index finger may be more calloused than a middle finger, and the more calloused finger will typically have thicker skin. By adjusting the depth of puncture so that the depth is no greater than necessary for extracting a required amount of blood, any pain experienced by the user may be minimized.

Lancets having an adjustable tip are known per se. For example, U.S. Pat. No. 4,469,110 to SLAMA discloses a mechanism which adjusts the penetration depth by rotating a threaded sleeve relative to a body. The SLAMA device is characterized as a "single bottom" device which employs a threaded design which can be expensive to manufacture. Moreover, such a device may require the user to rotate the threaded sleeve up to 360 degrees and more in order to attain the proper depth setting. Further, such a threaded resign is prone to inadvertent setting changes since there is nothing but frictional engagement between the mating threads to maintain the adjustment setting.

U.S. Pat. No. 4,895,147 to BODICKY et al. functions in a similar manner to the device in SLAMA and therefore suffers from similar disadvantages.

U.S. Pat. Nos. 5,464,418, 5,797,942, 5,908,434, 6,156,051 and 6,530,937 to SCHRAGA also disclose similar lancet devices and are hereby incorporated herein by reference as though set forth in full herein.

As disclosed in U.S. Pat. No. 5,908,434, the lancet device has a body portion which encloses a lancet and a lancet firing mechanism. The lancet typically has a needle extending therefrom and is caused to move towards the tip of the device by a trigger or firing mechanism. The lancet device forces the needle, by virtue of the needle being fixed thereto, out of the device by some distance or depth so that the needle can penetrate the skin of the user. The function of this firing mechanism and the lancet body design is disclosed in each of U.S. Pat. Nos. 5,797,942 and 5,908,434. These Patents are incorporated by reference herein in their entirety and are therefore only briefly discussed herein.

What is needed is a lancet device which can accurately and precisely control the depth of penetration of the needle relative to the surface of the user's skin while also being easy to use. It is also desirable for the user to be able to use and adjust the depth penetrating setting with just one hand and/or with less effort that currently required with existing lancet devices.

Thus, while advances have been made, there is a continuing need for a lancet device which provides for convenient, reliable and easy adjustment of penetration depth.

SUMMARY OF THE INVENTION

According to one aspect of the invention there is provided a lancet device that includes a body. A trigger is mounted to the body. A front cover includes a skin engaging end that includes a lancet opening through which a lancet needle extends. A holding member is movably mounted within the body and comprises a front end and a rear end. The front end is configured to receive a lancet. A stop surface moves with the holding member. A cam disk includes cam surfaces which can be contacted by the stop surface. The cam disk is configured to rotate at least partially. The cam disk rotates about an axis that is not parallel to an axis running through at least one of the lancet opening and the holding member.

The lancet device may further comprise a back cap configured to move between a retracted position and an original position. The back cap may be configured to move the holding member to a retracted position. The back cap may be coupled to a surface that engages the rear end of the holding member. The back cap may be coupled to an inner sleeve that includes a surface that engages the rear end of the holding member. The inner sleeve may comprise an opening that receives a rear end of the holding member. The back cap may be coupled to an inner sleeve that includes a surface that engages projections disposed on the rear end of the holding member.

The lancet device may further comprise a spring for biasing the back cap towards an original position. The lancet device may further comprise a first spring for biasing the holding member towards an extended position and a second spring for biasing the holding member in an opposite direction. The first and second springs may be arranged within an axial opening of the holding member. The first spring may contact one side of a projection extending inwardly from the body and wherein the second spring may contact another side of the projection. The projection may extend into an elongated slot formed in the holding member.

The lancet device may further comprise an end plug mounted to the rear end of the holding member. The first spring may be disposed between the projection and an inner wall surface arranged in the area of the front end of the holding member and wherein the second spring is disposed between the projection and the end plug. The trigger may be movably mounted to the body. The front cover may be removably mounted to the body. The holding member may comprise a projection that includes the stop surface. The holding member may comprise an integrally formed projection that includes the stop surface. The front end may comprise an opening that is configured to removably receive the lancet.

The lancet device may further comprise a deflecting member configured to be deflected by the trigger. The deflecting member may be coupled to the holding member. The deflecting member may comprise a first stop surface that contacts a first surface of a holding projection extending inwardly from the body. The deflecting member may comprise a second stop surface that contacts a second surface of the holding projection. The cam disk may comprise indicia. The cam surfaces may be arranged on a cam section of the cam disk, the cam section being disposed on a side of the cam disk that is opposite a side that includes the indicia. The cam disk may comprise a centrally disposed opening that is mounted to a journal within the body. The journal may be coupled to the body. The journal may extend inwardly from the body. The journal may comprise a center axis that is generally perpendicular to the axis running through the holding member. The cam disk may rotate about an axis that is generally perpendicular to an axis running through at least one of the lancet opening and the holding member. The cam disk may be disposed between the trigger and a back cap. The body may comprise a two piece body. The cam disk may be coupled to one of the two pieces of the two piece body. The front cover may be removably mounted to the two piece body. The lancet device may further comprise a back cap movably mounted to the two piece body. The body may comprise at least one curved side indentation through which the cam disk protrudes. The body may comprise two oppositely arranged curved side indentations through which portions of the cam disk protrude. The body may comprise a mechanism for viewing indicia of the cam disk. The mechanism for viewing indicia of the cam disk may comprise an opening. The lancet device may further comprise a retaining element for one of axially retaining the cam disk and securing the cam disk to the body.

The invention also provides a method of puncturing a surface of skin using the lancet device described above, wherein the method comprises adjusting a set depth of penetration of the needle by moving the cam disk to a desired set position, disposing the skin engaging end of the lancet device against a user's skin, and triggering the trigger to cause the lancet needle to penetrate the user's skin, wherein the puncture allows a blood sample to be taken.

The invention also provides a method of using the lancet device described above, wherein the method comprises rotating the cam disk to a desired set position, moving the holding member to a retracted position, maintaining the holding member in the retracted position until the trigger is triggered, disposing the skin engaging end of the lancet device against a user's skin, and triggering the trigger to cause movement of the holding member.

The invention also provides a lancet device, that includes a body, a trigger, a front cover comprising a skin engaging end that includes a lancet opening through which a lancet needle extends. A holding member is movably mounted within the body and comprises a front end and a rear end. The front end is configured to receive a lancet. A stop projection is coupled to the holding member. A cam disk comprises indicia and cam surfaces which can be contacted by the stop projection. The cam disk is configured to rotate at least partially. The cam disk is mounted to a projection that extends inwardly from the body.

The invention also provides a lancet device comprising a body, a trigger, a front cover comprising a skin engaging end that includes a lancet opening through which a lancet needle extends. A holding member is movably mounted within the body and comprises a front end and a rear end. The front end is configured to receive a lancet. A back cap is configured to move the holding member to a retracted position. A stop surface is coupled to the holding member. A cam disk is at least partially arranged within the body. The cam disk comprises indicia and cam surfaces which can be contacted by the stop projection. The cam disk is configured to rotate at least partially. The cam disk protrudes from at least one side wall of the body.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 5 shows a side cross-section view of the embodiment shown in FIG. 1. The device is shown in the loaded (trigger set) position after it has been so positioned by a trigger setting mechanism;

FIG. 6A shows a top view of the embodiment shown in FIG. 1;

FIG. 6B shows a side view of the embodiment shown in FIG. 6A;

FIG. 6C shows a front view of the embodiment shown in FIG. 6B;

FIG. 9A shows a top cross-section view of the front cover of the lancet device shown in FIG. 1;

FIG. 9B shows a top view of the front cover shown in FIG. 9A;

FIG. 9C shows a side cross-section view of the front cover shown in FIG. 9A;

FIG. 9D shows a side view of the front cover shown in FIG. 9A;

FIG. 9E shows a partial front view of the front cover shown in FIG. 9A;

FIG. 9F shows an enlarged view of the circled portion shown in FIG. 9C;

FIG. 10A shows a rear end view of the back cap (trigger setting cap) of the lancet device shown in FIG. 1;

FIG. 10B shows a side view of the back cover shown in FIG. 10A;

FIG. 10C shows a side cross-section view of the back cap shown in FIG. 10B;

FIG. 10D shows an enlarged view of the circled portion shown in FIG. 10C;

FIG. 10E shows a top view of the back cap shown in FIG. 10B;

FIG. 10F shows a top cross-section view of the back cap shown in FIG. 10E;

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
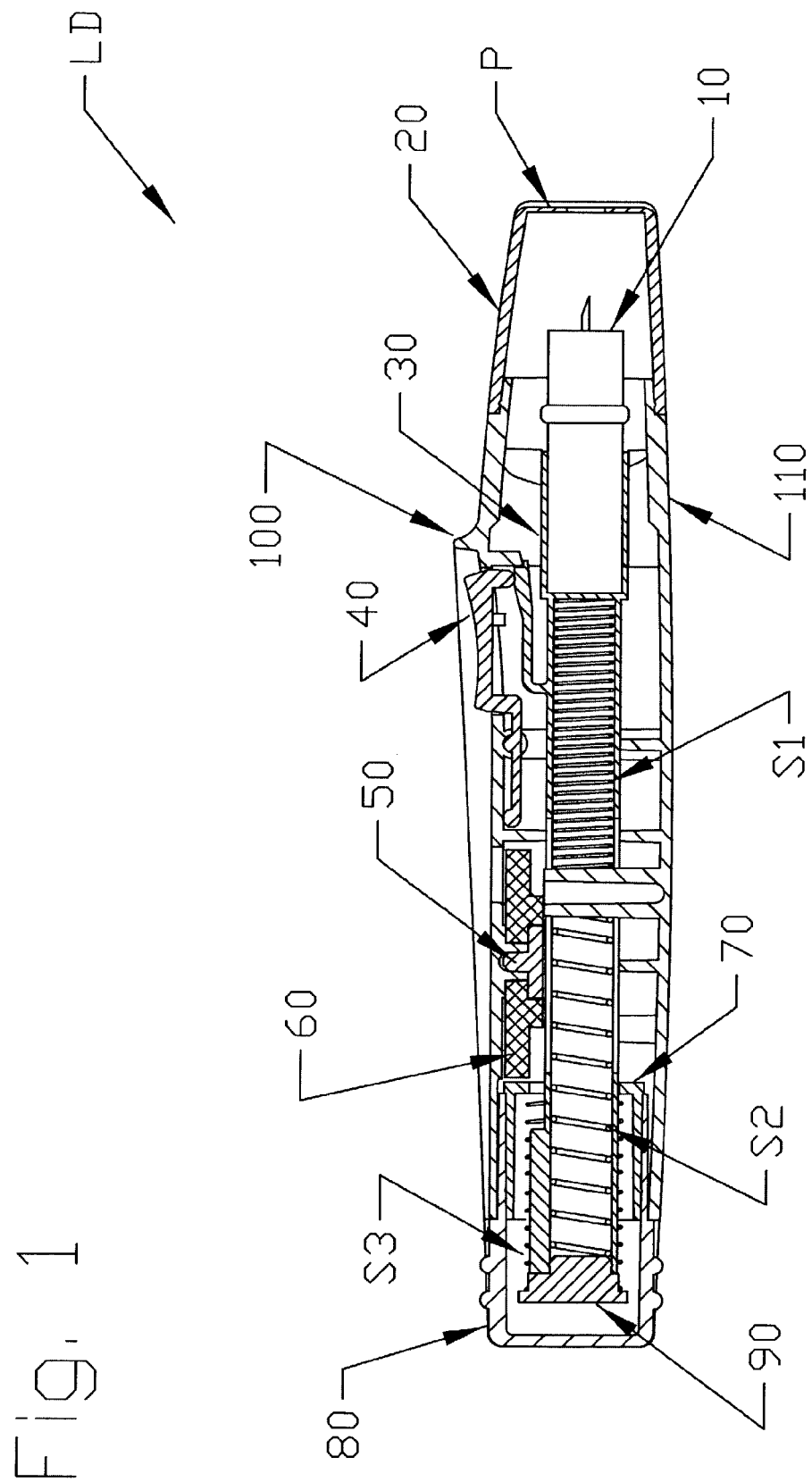
FIG. 1 shows a side cross-section view of one embodiment of the lancet device. The device is shown in the loaded (trigger set) position. The lancet is not shown in cross-section.

FIG. 1 shows a side cross-section side view of one embodiment of lancet device (the lancet 10 is not shown in cross-section). Lancet device LD has a lancet body made up of an upper body portion 100 and a lower body portion 110. These parts 100 and 110 are connected, e.g., using adhesives and/or fasteners and/or welding and/or snap-together holding mechanisms (not shown) to each other when the lancet device is initially assembled. A holding member 30 is movably disposed within the body parts 100, 110. Also, a front cover 20 is removably connected or attached to a front portion of the body parts 100, 110. By removing the front cover 20, one can gain access to the lancet 10. The lancet 10 can thus be removed and replaced with a new lancet 10 as necessary, once the front cover 20 is removed. As in many prior art lancet devices, the lancet device defines a plane P which is configured to contact (i.e., be positioned against) a user's skin. However, unlike known lancet devices, the instant embodiment may utilize an inwardly curved surface plane P beyond which the lancet need can extend. Next, a back cap 80 is arranged at a rear portion of the body parts 100, 110. The back cap 80 has a rear portion that can be gripped by a user and a front portion that slides within the body parts 100, 110. An inner sleeve 70 is connected (after being slid into the back cap 80) to the back cap 80 upon assembly of the lancet device. Movement of back cap 80 rearwardly causes the holding member 30 to retract until it reaches the loaded position shown in FIG. 1, as will be described in more detail later on. The lancet 10 itself is conventional and includes a needle. It can be replaced, as is the case in many prior art lancet devices. To ensure that lancet 10 is securely (yet removably) retained within the lancet device, the holding member 30 includes a lancet holding end which receives the lancet 10 therein.

As can be seen in FIG. 1, the holding member 30 preferably has three springs mounted thereto. In this regard, a first spring S1, which can be made of spring steel, is arranged within the holding member 30, just behind the lancet receiving portion. This spring S1 causes (and/or biases) the holding member 30 to move towards an extended position once a trigger 40 is activated. The trigger 40 includes a portion that is arranged within the body part 100 and is also mounted to upper body part 100. The trigger 40 also has a finger engaging (e.g. push button) portion that can be pushed into the lancet device. The trigger 40 functions as a spring in that it is capable of deflecting inwards (see FIG. 2) when force is applied to the finger engaging portion, and also capable of returning to a pre-deflection position (see FIGS. 1 and 3). A second spring S2, which can be made of spring steel, is also arranged within the holding member 30, but behind the first spring S1. This spring S2 causes (and/or biases) the holding member 30 to move back towards a retracted position once the lancet 10 reaches the extended position. In this way, the lancet 10 (and holding member 30) is automatically retracted after puncturing the skin of a user. A third spring S3, which can also be made of spring steel, is externally mounted to a rear portion of the holding member 30. This spring S3 causes (and/or biases) the back cap 80 (and attached inner sleeve 70) to move inwardly withing body parts 100, 110. When a user wishes to place the lancet device in the loaded position (see FIG. 1), a user need only move back cap 80 rearwardly (see FIG. 5). This in turn compresses the third spring S3 to a certain extent. However, when the user releases the back cap 80, spring S3 causes the back cap 80 to return to the position shown in FIGS. 1-4.

The lancet device LD also utilizes a cam disk 60 to adjust the penetration depth of the lancet needle. The cam disk 60 is preferably mounted to the upper body part 100 so as to be at least partially rotatable in each of two directions. Of course, the cam disk 60 can be mounted within the body in any desired manner provided it functions properly. To ensure that the cam disk 60 is axially retained to body part 100, yet allowed to rotate with respect to upper body part 110, a retaining member 50 is utilized. As will be more fully described in detail later on, the cam disk 60 has a plurality of cam surfaces 60e1-60e8 (see FIG. 16C) which are configured to be engaged by a stop projection 30j (in particular stop surface 30i of stop projection 30j) that is formed on or coupled to the holding member 30. Finally, the lancet device LD also utilizes an end plug 90 that ensures that the spring S2 is retained within the holding member 30.

Figure 2:
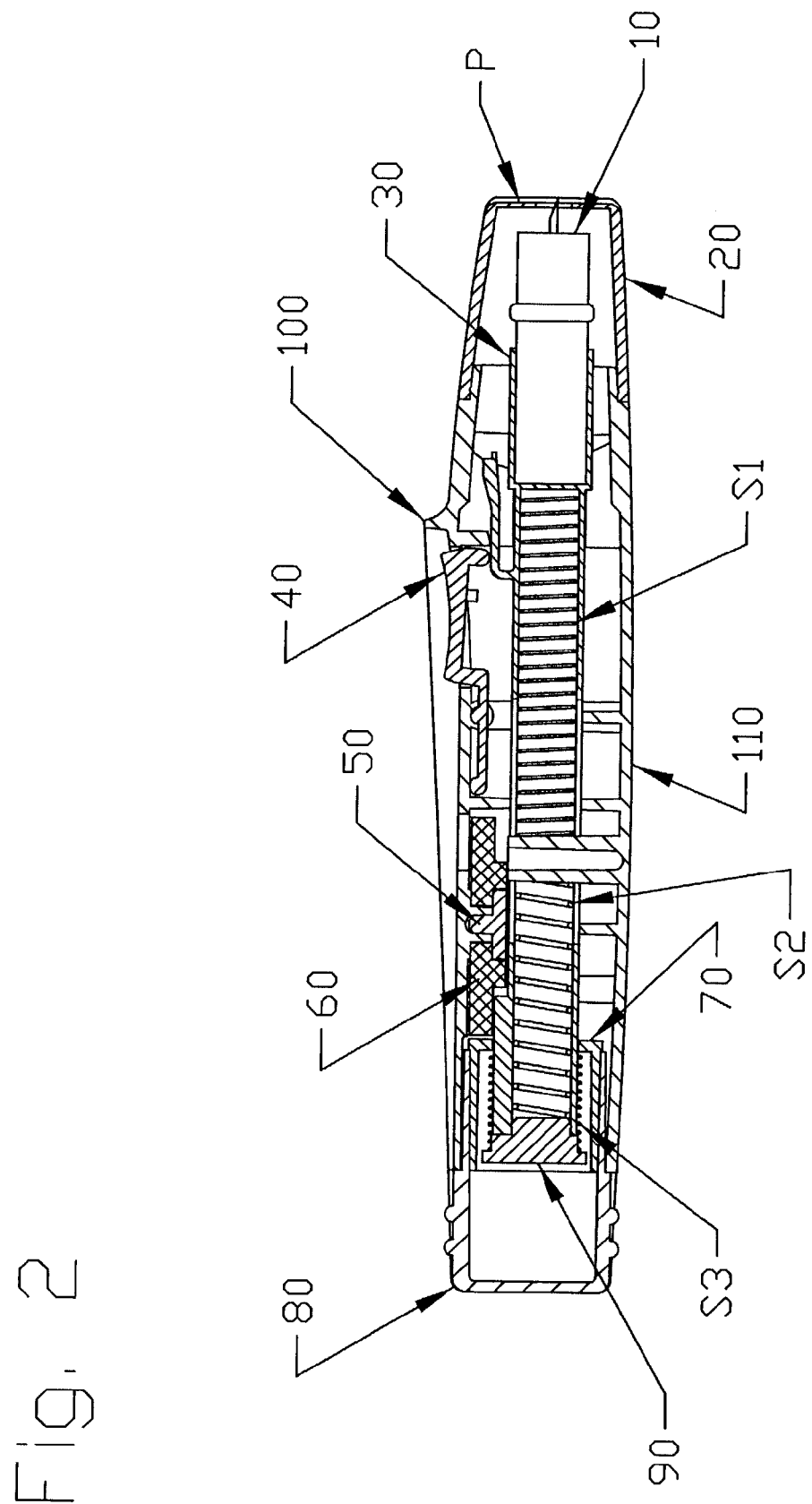
FIG. 2 shows a side cross-section view of the embodiment of FIG. 1. The device is shown with the lancet needle moving toward a pre-set depth position after it has been triggered.

As described above, FIG. 1 shows the lancet device LD with the lancet member 30 in the loaded position, i.e., ready to move to an extended position when the trigger 40 is pressed. The holding member 30 retains the loaded position of FIG. 1 as a result of engagement between a deflecting member 30c and a shoulder 100i of the upper body part 100. On the other hand, FIG. 2 shows what happens when the trigger 40 is pressed, i.e., the trigger 40 is caused to be deflected inwardly. That is, the holding member 30 is released from the loaded position of FIG. 1 and is caused to move towards plane P. This occurs because the trigger 40 causes the deflecting member 30c to disengage from the shoulder 100i of the upper body part 100. As discussed above, this movement is caused by the expansion (in the direction of a the axis of the holding member 30) of first spring S1. The holding member 30 continues to move towards the plane P until the stop projection 30j contacts or engages one of the stop surfaces 60e1-60e8 of the cam disk 60. Once the trigger 40 is released (once a user stops pressing on the trigger 40), the trigger 40 preferably moves back (e.g., automatically) to an un-deflected state shown in FIG. 3. The lancet device is then ready to be reloaded, i.e., it can then be placed back into the position shown in FIG. 1.

Figure 3:
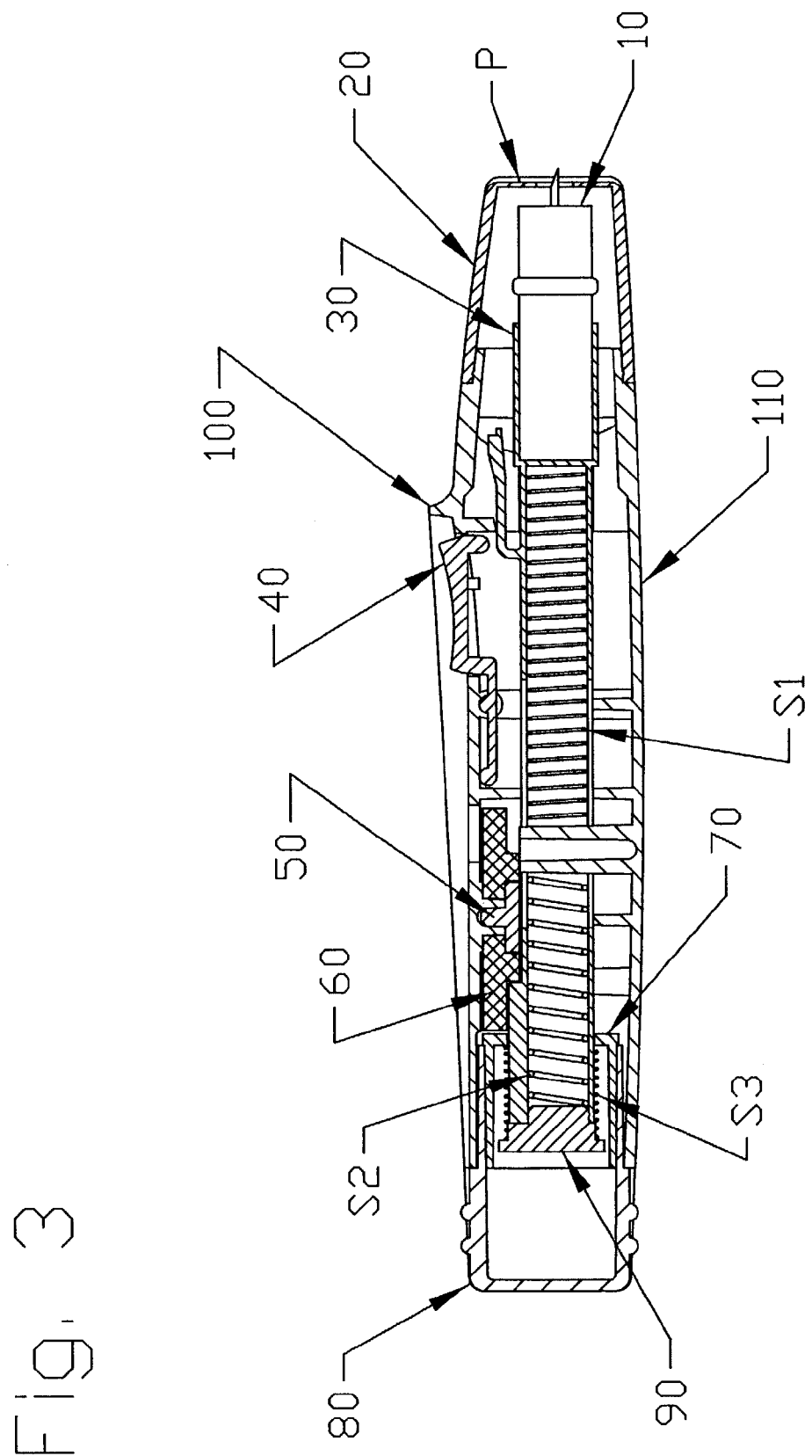
FIG. 3 shows a side cross-section view of the embodiment shown in FIG. 1. The device is shown with the lancet needle at a pre-set depth position.

FIG. 3 shows the lancet device with the holding member 30 in one of the pre-set extended positions, i.e., in one of the extended positions that will cause a desired puncture depth in the skin of a user (not shown). The distance that the lancet needle projects past plane P is thus determined by rotating the cam disk 60 until the desired setting is reached. This setting, in turn, causes a particular stop surface (i.e., one of surfaces 60e1-60e8) to be placed in the path of the stop projection 30j. The various stop surfaces (e.g., 8 surfaces shown in FIGS. 16A-D) of the cam disk 60 thus determine how much the holding member 30 will move in the extended position relative to the plane P. In this regard, FIG. 3 shows contact between the stop projection 30j and one of the surfaces 60e1-60e8 of the cam disk 60. FIG. 3 also shows the needle tip projecting through the opening in the front cover 20 and past the plane P. And, as discussed above, the trigger 40 has returned to a non-deflected original position.

Figure 4:
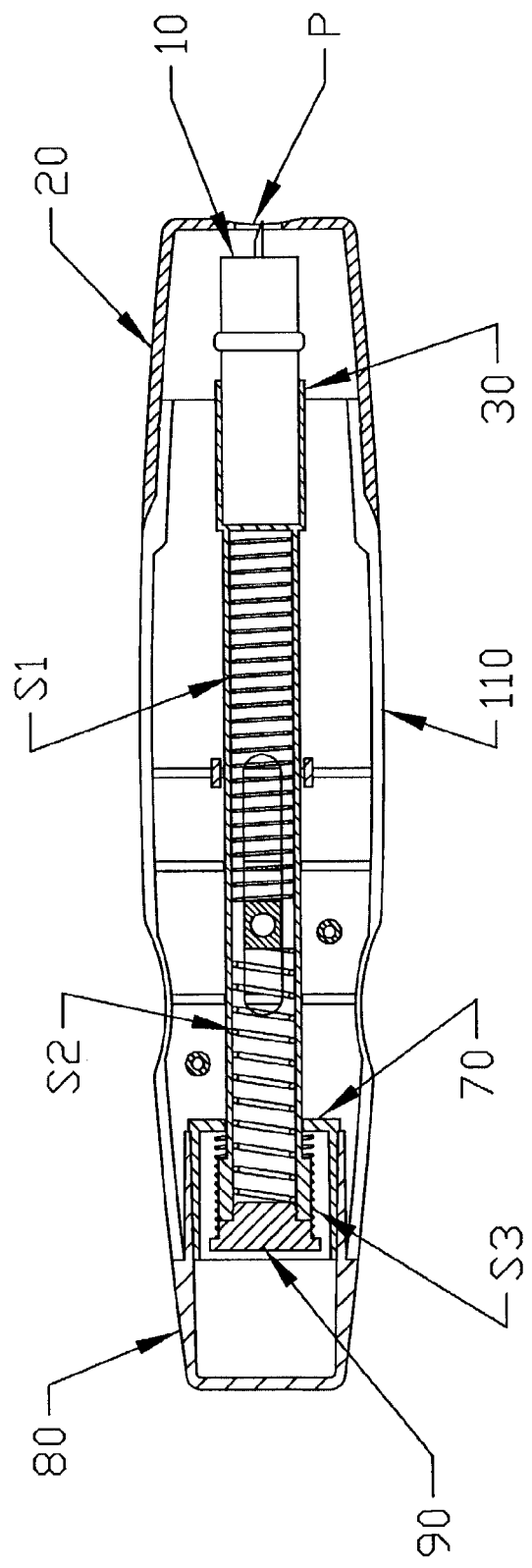
FIG. 4 shows a top cross-section view of the embodiment shown in FIG. 1 and in the position shown in FIG. 2.

FIG. 4 shows a top cross-section view of the lancet device of FIG. 1. In this regard, the holding member 30 is in the position shown in FIG. 2. As this figure illustrates, the upper body part 100 has been removed to expose a top view of the lower body part 110. As in FIGS. 1-3, the front cover 20, back cap 80, inner sleeve 70, end plug 90, holding member 30 and lancet 10 can be seen in their installed and/or assembled position. However, this figure allows one to more clearly see that the first spring S1 is arranged within the holding member 30, just behind the lancet receiving portion. The first spring S1 is preferably sized to slide into an internal opening 30p of the holding member 30. More particularly, the first spring S1 is preferably disposed inside the holding member 30 and between an inner wall 30n (Just behind lancet 10) of the holding member 30 and a projecting guide member 110h of the lower body part 110. That is, the first spring S1 is axially retained between a right side surface of projecting guide member 110h and the inner wall 30n of the holding member 30. As a result, the first spring S1 is caused to be compressed when the holding member 30 is moved back (i.e., to the left) to a retracted position relative to the lower body part 110. The projecting guide member 110h does not move because it is fixed to the lower body portion 110. Of course, the projecting guide member 110h can be arranged and/or mounted within the body in any desired manner provided it functions for its intended purpose. As discussed above, the first spring S1 causes (and/or biases) the holding member 30 towards an extended position once a trigger 40 (not shown in FIG. 4) is activated. As a result, the holding member 30 cannot be moved back to a retracted position without causing the first spring S1 to be compressed thereby.

The second spring S2 is also preferably sized to slide into an internal opening 30p of the holding member 30. More particularly, the second spring S2 is disposed inside the holding member 30 and between an inner wall 90a of the end plug 90 and the projecting guide member 110h of the lower body part 110. That is, the second spring S2 is axially retained between a left side surface of projecting guide member 110h and the inner wall 90a of the end plug 90. The second spring S2 is caused to be compressed when the holding member 30 is moved forward (i.e., to the right) to an extended position relative to the lower body part 110. Again, the projecting guide member 110h does not move because it if fixed to the lower body portion 110. As discussed above, the second spring S2 causes (and/or biases) the holding member 30 towards a retracted position once the holding member 30 reaches the various pre-set extended positions (see e.g., FIG. 3). Thus, the second spring S2 is compressed when the holding member 30 is extended by the first spring S1. Spring S2 then expands axially to retract the holding member 30. In this way, the lancet needle only momentarily projects past the plane P in the extended position before it is caused to retract back into the lancet device by the second spring S2. As a result, the lancet needle only projects past or beyond the plane P for a very brief time (i.e., a fraction of a second when the trigger 40 is pressed) and is otherwise not exposed to a user while the front cover 20 is installed thereon. Accordingly, a user or other innocent bystanders can be protected from being injured unintentionally by an exposed needle.

The third spring S3 is preferably sized to slide over a rear end of the holding member 30. More particularly, the third spring S3 is disposed over a rear end of the holding member 30 and between an inner wall 70p of the inner sleeve 70 and an annular shoulder 90c of the end plug 90. That is, the third spring S3 is axially retained between a left side inner surface 70p of the inner sleeve 70 and the annular shoulder 90c of the end plug 90. As a result, the third spring S3 is caused to be compressed when the back cap 80 is moved rearward (i.e., to the left as in FIG. 5) to an extended position relative to the upper and lower body parts 110, 110 (see FIG. 1). As discussed above, the third spring S3 causes (and/or biases) the back cap 80 towards a retracted position once a user releases the back cap 80 (compare FIG. 5 to FIG. 1). Thus, the third spring S3 is compressed when the back cap 80 is pulled backwards to cause the deflecting member 30c to seat onto the shoulder 100*i* (adjacent the trigger 40) of the upper body part 110. The third spring S3 then expands axially to cause the back cap 80 to move to the right until shoulders 80*p* of the back cap 80 contact end edges 100*b*, 110*b* of the upper and lower body parts 110, 110. However, the spring S3 does not compress completely. This is because the left side inner surface 70*b* of inner sleeve 70 contacts two oppositely arranged projections 30*g*, 30*h* of the holding member 30.

FIG. 5 shows another cross-section side view of the lancet device LD shown in FIG. 1 (the lancet 10 is not shown in cross-section). In FIG. 5, the back cap 80 is shown in the extended position. As described above, this movement is used to retract the holding member 30 until the deflecting member 30*c* engages the shoulder 100*i* of the upper body part 100. At this point, the user need only release the back cap 80 so that the third spring S3 will automatically cause the back cap 80 to move or retract towards the lancet device until it assumes the position shown in FIG. 1. As can be seen when comparing FIGS. 2 and 5, the first spring S1 becomes compressed axially when the back cap 80 causes the holding member 30 to move to a retracted position. As a result, the second spring S2 expands axially (see FIGS. 2 and 5), while the third spring S3 compresses axially (see FIG. 5). However, once the back cap 80 is released, the third spring S3 expands axially—which causes the back cap 80 (and the attached inner sleeve 70) to retract back into the lancet device (see FIG. 1).

FIGS. 6A-C show top, side and front views of the lancet device LD shown in FIGS. 1-5. As discussed above, the lancet device has a lancet body made up of an upper body portion 100 and a lower body portion 110. These parts 100 and 110 are connected to each other when the lancet device is initially assembled. In this regard, a seam line SL is preferably formed and/or provided between the bottom edges of the upper body part 100 and the top edges of the lower body part 110. The front cover 20 is preferably removably connected or attached to a front portion of the body parts 100, 110. In this way, one can gain access to the lancet 10. The lancet 10 can thus be removed and replaced with a new lancet 10 as necessary, once the front cover 20 is removed (not shown). As in many prior art lancet devices, the lancet device defines a plane P which is configured to contact (i.e., be positioned against) a user's skin. However, unlike known lancet devices, the instant embodiment uses an inwardly curved surface as the plane P beyond which the lancet need can extend. As is shown in FIG. 6C, the curved surface plane P has a lancet opening LO through which the lancet needle passes. The back cap 80 is arranged at a rear portion of the body parts 100, 110. The back cap 80 preferably has a rear portion with projecting tabs 80*j* (i.e., two on each side of the back cap). These tabs 80*j* allow a user to more easily grip the back cap 80. As discussed above, movement of back cap 80 rearwardly (as in FIG. 5) causes the holding member 30 to retract until it reaches the loaded position shown in FIG. 1.

Again, with reference to FIGS. 6A-C, the trigger 40 preferably has a tear-drop shaped button which can be pressed by a user to cause the lancet 10 to move to the extended position. The cam disk 60 can be seen to project partially from opposite recessed portions of the upper and lower body parts 100, 110. In this regard, the recesses preferably have curved inner surfaces whose radii are greater than a radius of the cam disk 60. In order to allow the user to see which cam surface (one of surfaces 60*e*1-60*e*8) is arranged in the path of the stop projection 30*j* (i.e., to adjust the desired depth setting) the upper body part 100 has a window W (e.g., a through opening) through which one can read the indicia (e.g., numbers or other desired indicia such as letters or marks) of the cam disk 60. As should be evident, the lancet device is configured with curved surfaces and an ergonomic shape to enable a user to grip the device more securely, while also being able to rotate the cam disk 60 with one or more fingers of the same hand. Unlike the devices of the prior art, one can adjust the depth of penetration without using both hands. Of course, some users may require two hands to place the lancet device in the loaded position, since they may not be able to pull the back cap 80 backwards without using both hands.

Also notable from FIGS. 6A-C, the upper body part 100 preferably has an upper inclined and/or slightly curved projecting edge PE. The advantage of this edge PE is that it protects the trigger 40. That is, it acts to prevent unintentional activation of the trigger 40. This is because the trigger 40 is positioned beneath the edge PE so that inadvertent contact with of the upper body part 100 will not cause unintentional movement of the trigger 40.

To ensure that there is a smooth transition between the various parts of the lancet device, certain edges are preferably made to have a curved and/or profiled arrangement. Thus, the front cover 20 has circular or curved upper and lower edges (see also FIGS. 9A-B) and complex profile side edges (see also FIGS. 9C-D). Similarly, the upper and lower body parts 100, 110 have top and bottom shoulder edges which are shaped to correspond to the circular or curved upper and lower edges of the front cover 20. The upper and lower body parts 100, 110 also have side shoulder edges which are shaped to correspond to the side complex profile edges of the front cover 20. The back cap 80 has straight upper, lower and side shoulder edges (see also FIGS. 10B and E). Similarly, the upper and lower body parts 100, 110 preferably have rear top, bottom and side straight edges which are shaped to correspond to the straight shoulder edges of the back cap 80. Additionally, the external surfaces of both the back cap 80 and the front cover 20 have an arrangement and/or configuration which continues the curved external surfaces of the upper and lower body parts 100, 110.

FIGS. 7A-D show top, side cross-section, bottom and front views of the upper body part 100. The upper body part 100 can preferably be made as one-piece structure by e.g., injection molding. In this regard, it is preferably made of a plastic or synthetic resin such as, e.g., ABS plastic. The upper body part 100 may also have be made of ABS—Metallic Silver and have a finish designated as SPI-A2. Additionally, the upper body part 100 may have an overall length that is approximately 2.9" (i.e., between edges 100*a* and 100*b*). This will ensure that the assembled lancet device can have an overall length of approximately 4.1". Of course, other materials and/or finishes may be utilized, without leaving the scope of the invention. Moreover, the upper body part 100 may even be made of a plurality of sections of parts which are joined together to form the complete upper body part 100, without leaving the scope of the invention.

The upper body part 100 preferably has a front straight edge 100*a* and includes a circular and/or curved shoulder 100*a*1. The radius of this shoulder 100*a*1 may be approximately 0.4". As will be described later on with regard to FIG. 9, the front edge 100*a* is configured to slide within wall 20*c* until contact occurs between circular and/or curved edge 20*h* and shoulder 100*a*1. A continuous projection 100*a*2 is disposed between front edge 100*a* and shoulder 100*a*1. This projection 100*a*2 has a rounded edge that is configured to fit within or otherwise engage a continuous indentation or recess 20*i* (see FIGS. 9A, 9C and 9F). In this regard, the recess 20*i* similarly has a rounded bottom that corresponds to the rounded edge of projection 100*a*2. Of course, the projection 100*a*2 need not be continuous, i.e., it does not have to extend continuous from side 100*c* to side 100*d*. It can instead be formed as intermitted projections or it may have the form of a single short projection that is centrally arranged with respect to walls 100c and 100d. Alternatively, the body part 100 can have the recess while the front cap 20 has the projection. Of course, other connecting mechanisms, whether conventional or otherwise, may also be utilized in place of the projection and recess connection.

The upper body part 100 also has a curved projecting edge PE which has already been described. This edge PE extends to the rear edge 100b, and may have a radius of approximately 108" and/or may be essentially straight. Arranged within the curved projecting edge PE is a tear-drop shaped through opening 100g. This opening 100g is sized and configured to receive the push button portion 40a of the trigger 40 (see FIG. 14). Of course, the opening 100g can have any desired size, shape or configuration provided it allows a user access to the trigger 40 and provided that it generally corresponds to the size, shape and configuration of the trigger 40. The opening 100g is formed in an upper wall near an inwardly projecting shoulder 100i. As was described previously, this shoulder 100i is sized, shaped and/or configured to be engaged by the deflecting member 30c (see FIG. 15). In this regard, the projection 100i has a straight contact surface that is generally parallel to edges 100a and 100b and a bottom surface or edge that can range from being generally parallel (relative to the bottom straight edges of sides 100c and 100d) to being tapered or angled by as much as 15 degrees or more. As will be described later on with regard to FIG. 15, the straight contact surface of projection shoulder 100i is configured to be engaged by surface 30c1 of deflecting member 30c and the bottom edge of projection shoulder 100i is configured to be engaged by portion 30c2 of the deflecting member 30c.

The upper body part 100 additionally preferably includes two plate-like projections 100h which are generally centrally disposed relative to sides 100c and 100d. The purpose of these projections 100h is to help guide the deflecting member 30c of the lancet holder 30 along a linear path. These projections 100h may also prevent the holding member 30 from rotating within the lancet device. In this regard, the projections 100h are spaced apart a distance that is slightly greater than a width of deflecting member 30c (see FIG. 15A). By ensuring that the projections 100h are spaced apart by an amount that is greater than a width of the deflecting member 30c, the holding member 30 can be allowed to move forward and backwards with the lancet device without rotating. Two C-shaped projections 100j also extend inwardly from the wall of the upper body part 100. These projections 100j form an upper half portion of a bearing system for the trigger 40. Together with the lower projections 110g (see FIG. 8), i.e., lower half portion of the bearing system, the parts 100j and 110g form two circular bearing supports for the trigger 40. As will be described later on with regard to FIG. 14, the journal elements 40c of the trigger 40 are mounted to the bearing supports 100j/110g. The upper body part 100 additionally preferably includes a connecting rib 100k that provides strength to the upper body part 100. In order to allow the holding member 30 move freely within the lancet device and without being obstructed by the rib 100k, a circular or curved recess (see FIG. 7D) is formed in the center of the rib 100k. This recess of the rib 100k can have a radius of approximately 0.15".

The upper body part 100 further preferably includes a circular bearing journal 1001 that is generally centrally disposed relative to sides 100c and 100d. The purpose of this journal 1001 is to provide a rotatable mounting for the cam disk 60 (see FIG. 16). The journal 1001 has a cylindrical outer surface on which an inner diameter 60b of cam disk 60 rotates. The journal 1001 also has an inner recess that includes a cylindrical portion and a rounded bottom end. The cylindrical portion of the recess is sized to receive (i.e., with frictional engagement) the slightly tapered projecting portion 50b of the retaining member 50 (see FIG. 12). A bearing surface 100m is arranged at a bottom end of the journal 1001. This surface 100m serves to axially retain surface 60g of the cam disk 60. On the other hand, once the retaining member 50 is assembled to journal 1001 so as to trap the cam disk 60 (see e.g., FIG. 1), the cam disk 60 becomes axially retained between the two surfaces 100m and 50d. Of course, the distance between surfaces 100m and 50d is made to be slightly greater than a thickness (measured between surfaces 60d and 60g) of the cam disk 60 so that the cam disk 60 can rotate somewhat freely, i.e., with reduced friction. This is also ensured if there is a slightly lose fit between the outer cylindrical surface of journal 1001 and the inner diameter 60b of cam disk 60. The bearing surface 100m also projects slightly from planar surface 100n of upper body part 100.

Figure 7A:
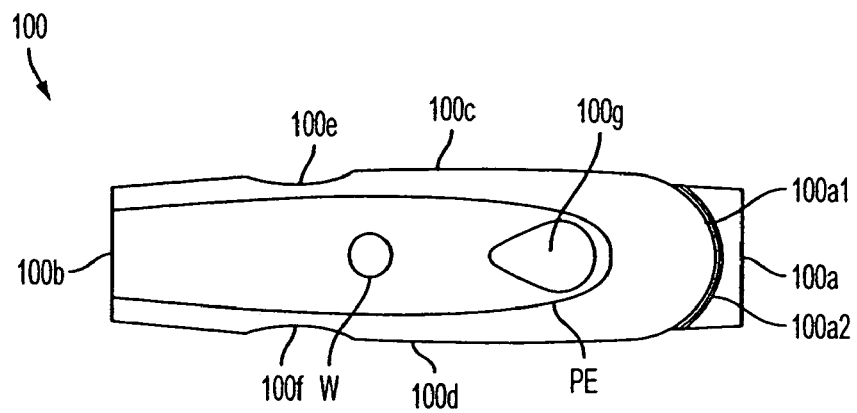
FIG. 7A shows a top view of the upper body part of the lancet device shown in FIG. 1.
Figure 7B:
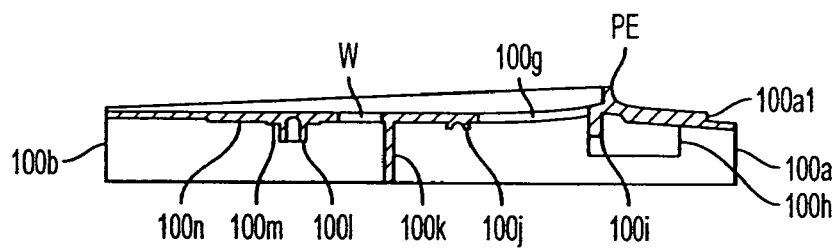
FIG. 7B shows a cross-section view of the upper body part shown in FIG. 7A.
Figure 7C:
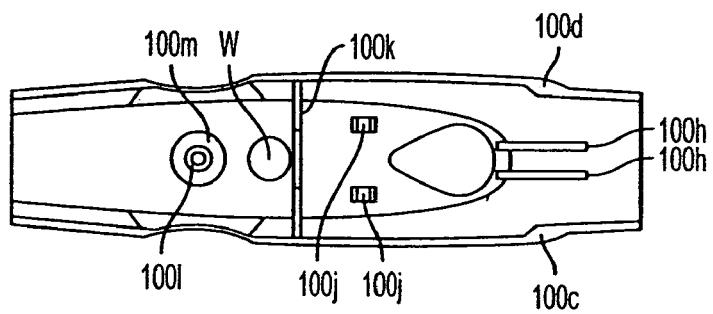
FIG. 7C shows a bottom view of the upper body part shown in FIG. 7A.
Figure 7D:
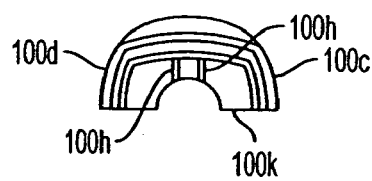
FIG. 7D shows a front view of the upper body part shown in FIG. 7A.

The upper body part 100 also includes circular or curved indented and/or recessed side portions 100e and 100f. These recesses 100e and 100f may have a radius of approximately 0.66". As described previously, these recessed portions allow a user to access the cam disk 60. That way, the user can use a finger to rotate the cam disk 60 from either side 100c or side 100d. As seen in FIG. 7D, the sides 100c and 100d can be curved outwardly (i.e., convex) and have a radius of approximately 0.6". The sides 100c and 100d can also preferably be curved outwardly in the length direction (i.e., see FIG. 7A) and have a radius of approximately 16.8". The rear edge 100b of the upper body part 100 is a continuous straight edge that is configured to make contact with shoulder 80p of back cap 80 (see FIG. 10).

FIGS. 8A-D show top, side cross-section, bottom and front views of the lower body part 110. The lower body part 110 can preferably be made as one-piece structure by e.g., injection molding. In this regard, it is preferably made of a plastic or synthetic resin such as, e.g., ABS plastic. The lower body part 110 may also have be made of ABS—Metallic Silver and have a finish designated as SPI-A2. Additionally, the lower body part 110 may have an overall length that is approximately 2.9" (i.e., between edges 110a and 110b). This will ensure that the assembled lancet device can have an overall length of approximately 4.1". Of course, other materials and/or finishes may be utilized, without leaving the scope of the invention. Moreover, the lower body part 110 may even be made of a plurality of sections of parts which are joined together to form the complete upper body part 110, without leaving the scope of the invention.

The lower body part 110 preferably has a front straight edge 110a and includes a circular and/or curved shoulder 110a1. The radius of this shoulder 110a1 may be approximately 0.4". As will be described later on with regard to FIG. 9, the front edge 110a is configured to slide within wall 20d until contact occurs between circular and/or curved edge 20h and shoulder 110a1. A continuous projection 110a2 is disposed between front edge 110a and shoulder 110a1. This projection 110a2 has a rounded edge that is configured to fit within or otherwise engage continuous indentation or recess 20i (see FIGS. 9A, 9C and 9F). In this regard, the recess 20i similarly has a rounded bottom that corresponds to the rounded edge of projection 110a2. Of course, the projection 110a2 need not be continuous, i.e., it does not have to extend continuous from side 110c to side 110d. It can instead be formed as intermitted projections or it may have the form of a single short projection that is centrally arranged with respect to walls 110c and 110d. Alternatively, the body part 110 can have the recess while the front cap 20 has the projection. Of course, other connecting mechanisms, whether conventional or otherwise, may also be utilized in place of the projection and recess connection.

The lower body part 110 also preferably has a curved bottom surface 110*l*. This surface 110*l* extends from the rear edge b to the shoulder 110*a*1 and may have a radius of approximately 31" and/or may be essentially straight. The lower body part 110 additionally preferably includes two plate-like projections 100*m* which are generally centrally disposed relative to sides 110*c* and 110*d*. The purpose of these projections 110*m* is to help guide the holding member 30 along a generally linear path. In this regard, the projections 110*m* are spaced apart a distance similar to projections 100*h* described with respect to FIG. 7. Two c-shaped projections 110*g* also extend upwardly from the wall of the lower body 110. A connecting rib 110*n* serves to connect the projections 110*g* to the bottom wall 110*l* and sides 110*c* and 110*d*. These projections 110*g* form a lower half of a bearing system for the trigger 40. Together with the upper projections 100*j* (see FIG. 7), i.e., upper half of the bearing system, the parts 100*j* and 110*g* form two circular bearing supports for the trigger 40. As will be described later on with regard to FIG. 14, the journal elements 40*c* of the trigger 40 are mounted to the bearing supports formed by parts 100*j* / 110*g*. The lower body part 110 additionally includes connecting ribs 110*i* and 110*k* that provides strength to the lower body part 110. In order to allow the holding member 30 move freely within the lancet device and without being obstructed by the ribs 110*i* and 110*k*, circular or curved recesses (see FIG. 8D) are formed in the center of the ribs 110*i* and 110*k*. These recesses of the ribs 110*i* and 110*k* can have a radius of approximately 0.15".

The lower body part 110 further preferably includes a rectangular shaped projection 110*h* that is generally centrally disposed relative to sides 110*c* and 110*d*. The purpose of this projection 110*h* is to guide the holding member 30 within the lancet device and to serve as stops for springs S1 and S2. The projection 110*h* has a polygonal (i.e., four sided) shaped outer surface. A left side surface of the projection 110*h* serves a contact surface for spring S2 (see e.g., FIG. 1). A right side surface of the projection 110*h* serves a contact surface for spring S1 (see e.g., FIG. 1). The projection 110*h* also has an inner recess that includes an inner tapered or conical portion and a rounded bottom end. This is so mainly for ease of manufacture and to reduce material costs. As can be seen from FIG. 1, the length of the projection 110*h* should not be so great so as to contact the cam disk 60. However, it should be of sufficient length so as to project through and slightly beyond the holding member 30.

The lower body part 110 preferably further includes two tapered or conical projections 110*j* that are generally arranged off-center relative to sides 110*c* and 110*d*. The purpose of these projections 110*i* is to frictionally engage the cam disk 60. Each projection 110*j* has a small rounded projection centrally disposed at an upper end. These rounded projections engage rounded indentations 60*h* of the cam disk 60 (see FIG. 16B) when the cam disk 60 is in a particular position.

Figure 8A:
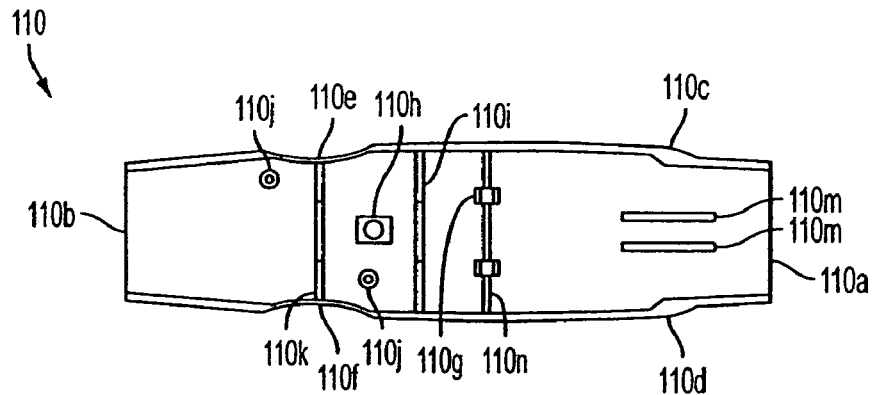
FIG. 8A shows a top view of the lower body part of the lancet device shown in FIG. 1.
Figure 8B:
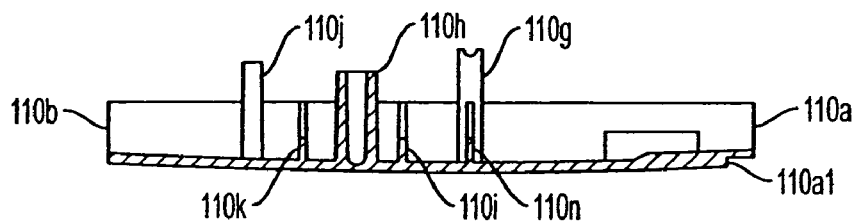
FIG. 8B shows a cross-section view of the lower body part shown in FIG. 8A.
Figure 8C:
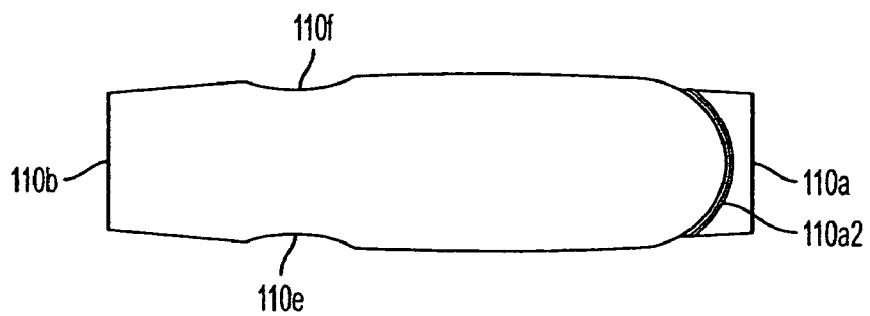
FIG. 8C shows a bottom view of the lower body part shown in FIG. 8A.
Figure 8D:
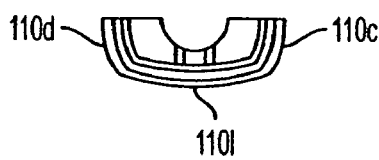
FIG. 8D shows a front view of the lower body part shown in FIG. 8A.

The lower body part 110 also preferably includes circular or curved indented side portions 110*e* and 110*f*. These recesses 110*e* and 110*f* may have a radius of approximately 0.66". As described previously, these recessed portions allow a user to access the cam disk 60. That way, the user can use a finger to rotate the cam disk 60 from either side 110*c* or side 110*d*. As seen in FIG. 8D, the sides 110*c* and 110*d* can be curved outwardly (i.e., convex) and have a radius of approximately 0.6". The sides 110*c* and 110*d* can also be curved outwardly in the length direction (i.e., see FIG. 8A) and have a radius of approximately 16.8". The rear edge 110*b* of the lower body part 110 is preferably a continuous straight edge that is configured to make contact with shoulder 80*p* of back cap 80 (see FIG. 10).

FIGS. 9A-F show top cross-section, top, side cross-section, side and partial front views of the front cover 20. The front cover 20 can preferably be made as one-piece structure by e.g., injection molding. In this regard, it is preferably made of a plastic or synthetic resin such as, e.g., ABS plastic. The front cover 20 may also have be made of ABS—Light Blue and have a finish designated as SPI-A2. Additionally, the front cover 20 may have an overall length that is approximately 2" (i.e., between edges 20*j* and 20*e*). This will ensure that the assembled lancet device can have an overall length of approximately 4.1". Of course, other materials and/or finishes may be utilized, without leaving the scope of the invention. Moreover, the front cover 20 may even be made of a plurality of sections of parts which are joined together to form the complete front cover 20, without leaving the scope of the invention.

The front cover 20 preferably has a front wall 20*e* that includes a circular and/or curved indentation 20*f* (i.e., defining plane P) and a centrally disposed through opening 20*g* (i.e., defining lancet opening LO). The radius of this indentation 20*f* may be approximately 1.1" and the diameter of the through opening 20*g* may be approximately 0.26". Of course, the invention also contemplates a plane P which is straight or which curves outwardly (not shown). As was described previously, the left edges of walls 20*a*, 20*b*, 20*c* and 20*d* are configured to slide over front edges 100*a* and 110*a* until contact occurs between circular and/or curved edges 20*h* and shoulders 100*a*1 and 110*a*1. A continuous indentation 20*i* is disposed within the front cap 20. This indentation 20*i* may have a radius of approximately 0.02" and a depth of approximately 0.009". As explained previously, this indentation 20*i* is configured to receive or otherwise engage with the continuous projections 100*a*2 and 110*a*2 (see FIGS. 7A and 8C). Of course, the recess 20*i* need not be continuous, i.e., it does not have to extend continuous. It can instead be formed as intermitted recesses or it may have the form of a single short recess on at least two opposite sides and that are centrally arranged with respect to walls 20*a*-20*d*. The side walls 20*a* and 20*b* also have rearward extending profiled walls 20*j*. These have a profiled edge that generally corresponds to the profiled side walls of body portions 100 and 110 (see FIG. 6B).

Side wall 20*a* is preferably tapered inwardly from edge 20*h* to surface 20*e* and formes a rounded corner (e.g.,with a radius of approximately 0.1") where wall 20*a* meets wall 20*e*. This wall 20*a* can be curved along its length (see FIG. 9B), having a radius of approximately 33.5", may also be curved outwardly (i.e., convex, see FIG. 9E) and may be formed by two curved surfaces. One curved surface may have a radius of approximately 1" and may extend from wall 20*c* towards wall 20*d*. Another curved surface may have a radius of approximately 1" and may extend from wall 20*d* towards wall 20*c*. These two surfaces may meet generally at the center of wall 20*a*. Side wall 20*b* is tapered inwardly from edge 20*h* to surface 20*e* and formed a rounded corner (e.g.,with a radius of approximately 0.1") where wall 20*b* meets wall 20*e*. This wall 20*b* can be curved along its length (see FIG. 9B), having a radius of approximately 33.5", may also be curve outwardly (i.e., convex, see FIG. 9E) and may be formed by two curved surfaces. One curved surface may have a radius of approximately 1" and may extend from wall 20*c* towards wall 20*d*. Another curved surface may have a radius of approximately 1" and may extend from wall 20*d* towards wall 20*c*. These two surfaces may meet generally at the center of wall 20*b*. Side wall 20c is tapered inwardly from edge 20h to surface 20e and formed a rounded corner (e.g.,with a radius of approximately 0.1") where wall 20c meets wall 20e. This wall 20c can be curved along its length (see FIG. 9D), having a radius of approximately 22", may also be curved outwardly (i.e., convex, see FIG. 9E), may be formed by one curved surface that has a radius of approximately 1.8" and may extend from wall 20a towards wall 20b. Side wall 20d is tapered inwardly from edge 20h to surface 20e and formed a rounded corner (e.g., with a radius of approximately 0.1") where wall 20d meets wall 20e. This wall 20d can be curved along its length (see FIG. 9D), having a radius of approximately 62" and may also be curved outwardly (i.e., convex, see FIG. 9E), may be formed by one curved surface that has a radius of approximately 1.9" and may extend from wall 20a towards wall 20b. The inner surface of wall 20e can be planar (see FIG. 9A).

FIGS. 10A-F show rear, side, side cross-section, top, and top cross-section views of the back cap 80. The back cap 80 can preferably be made as one-piece structure by e.g., injection molding. In this regard, it is preferably made of a plastic or synthetic resin such as, e.g., ABS plastic. The back cap 80 may also have be made of ABS—Light Blue and have a finish designated as SPI-A2. Additionally, the back cap 80 may have an overall length that is approximately 0.87" (i.e., between ends 80k and 80a). This will ensure that the assembled lancet device can have an overall length of approximately 4.1". Of course, other materials and/or finishes may be utilized, without leaving the scope of the invention. Moreover, the back cap 80 may even be made of a plurality of sections of parts which are joined together to form the complete back cap 80, without leaving the scope of the invention.

Figure 11A:
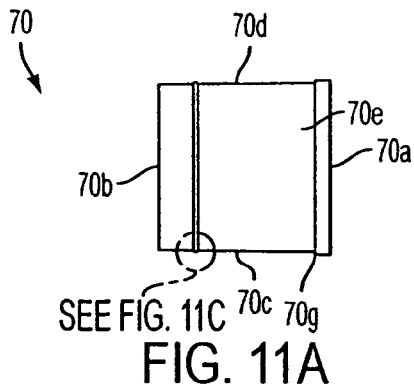
FIG. 11A shows a top view of the inner sleeve member of the lancet device shown in FIG. 1.
Figure 11B:
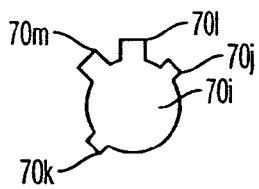
FIG. 11B shows a front view of the profiled opening of the inner sleeve member shown in FIG. 11A.
Figure 11C:
FIG. 11C shows an enlarged view of the circled portion shown in FIG. 11A.
Figure 11D:
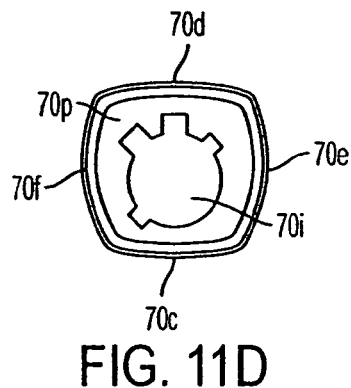
FIG. 11D shows a rear end view of the inner sleeve shown in FIG. 11A.
Figure 11E:
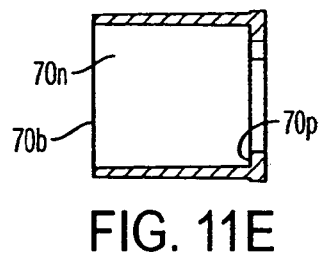
FIG. 11E shows a side cross-section view of the inner sleeve shown in FIG. 11A.

The back cap 80 preferably has a rear wall 80k that has a planar outer surface and a planar inner surface 80n. The back cap 80 has an opening 80l that extends from surface 80n to edge 80a. This opening 80l tapers outwardly towards edge 80a at an angle of approximately 0.5 degrees (per side). The width of the rectangular surface 80n (measured up and down in FIG. 10C) may be approximately 0.46" while the width of the surface 80n (measured up and down in FIG. 10F) may be approximately 0.49". As was described previously, the walls 80b-80e are configured to slide into rear edges 100b and 110b until contact occurs between the shoulder 80p and edges 100b and 110b. A continuous indentation 80m is disposed within the back cap 80. This indentation 80m may have a radius of approximately 0.007" and a depth of approximately 0.004". As will be explained later on with regard to FIG. 11, this indentation 80m is configured to receive or otherwise engage with the continuous projection 70h (see FIGS. 11A and 11C) of inner sleeve 70. Of course, the recess 80m need not be continuous, i.e., it does not have to extend continuous. It can instead be formed with intermitted recesses or it may have the form of a single short recess on at least two opposite sides and that are centrally arranged with respect to walls 80b-80e. Alternatively, the inner sleeve can have the recess while the back cap 80 has the projection. Of course, other connecting mechanisms, whether conventional or otherwise, may also be utilized in place of the projection and recess connection.

The side walls 80b-80e also preferably taper slightly from shoulder 80p to edge 80a by approximately 0.5 degrees (per side). The width of the rectangular edge at the bottom of the shoulder 80p (measured up and down in FIG. 10C) may be approximately 0.51" while the width of this edge (measured up and down in FIG. 10F) may be approximately 0.54". The width of the rectangular edge at the top of the shoulder 80p (measured up and down in FIG. 10C) may be approximately 0.6" while the width of this edge (measured up and down in FIG. 10F) may be approximately 0.61". Side walls 80f, 80g, 80h and 80i also taper slightly from the top of shoulder 80p to surface 80k. The approximately square shaped surface 80k has a length and width of approximately 0.5". However, the walls 80f, 80g, 80h and 80i may also be curved outwards slightly. In this regard, wall 80h may have a radius of approximately 108.3" (measured in the direction of the length shown in FIG. 10B) and may be outwardly curved with a radius of approximately 1" (see FIG. 10A). Wall 80i may have a radius of approximately 31" (measured in the direction of the length shown in FIG. 10B) and may be outwardly curved with a radius of approximately 1" (see FIG. 10A). Wall 80f may have a radius of approximately 16.7" (measured in the direction of the length shown in FIG. 10E) and may be outwardly curved by being formed by two curved surfaces each having a radius of approximately 0.5" and each extending from sides 80h and 80i (see FIG. 10A). Wall 80g may have a radius of approximately 16.7" (measured in the direction of the length shown in FIG. 10E) and may be outwardly curved by being formed by two curved surfaces each having a radius of approximately 0.5" and each extending from sides 80h and 80i (see FIG. 10A).

Side walls 80h and 80i also each preferably include two elongated projections 80j which extend outwardly therefrom. These projections 80j preferably have rounded ends and rounded edges. The purpose of these projections 80j is, of course, to ensure that a user can grip the back cap 80 when the lancet device is to be placed into the loaded position (see FIGS. 1 and 5). Of course, any desired gripping system can be utilized in place of the tabs 80j, such as, e.g., a knurl, a textured or a high friction surface.

FIGS. 11A-E show top, rear and side cross-section views of the inner sleeve 70. The inner sleeve 70 can preferably be made as one-piece structure by e.g., injection molding. In this regard, it is preferably made of a plastic or synthetic resin such as, e.g., ABS plastic. The inner sleeve 70 may also have be made of ABS—Light Blue and have a finish designated as SPI-C1. Additionally, the inner sleeve 70 may have an overall length that is approximately 0.47" (i.e., between edges 70a and 70b). This will ensure that the assembled lancet device can have an overall length of approximately 4.1". Of course, other materials and/or finishes may be utilized, without leaving the scope of the invention. Moreover, the inner sleeve 70 may even be made of a plurality of sections of parts which are joined together to form the complete inner sleeve 70, without leaving the scope of the invention.

The inner sleeve 70 has a front wall 70a that has a planar outer surface and a planar inner surface 70p. An opening 70i is provided in the wall 70a. This opening has a circular central part and four generally polygonal recesses 70j-70m. Recess 70j is approximately 0.05" wide and has a bottom surface that can be arranged approximately 0.15" from a center axis of the opening 70i. It is oriented at approximately 45 degrees to the horizontal. Recess 70k is arranged opposite (i.e., by 180 degrees) recess 70j and is also approximately 0.05" wide. This recess 70k has a bottom surface that can be arranged approximately 0.15" from a center axis of the opening 70i. Recess 70l is arranged offset (i.e., by approximately 45 degrees) from recess 70j and is approximately 0.07" wide. This recess 70l has a bottom surface that can be arranged approximately 0.18" from a center axis of the opening 70i. Recess 70m is arranged offset (i.e., by approximately 45 degrees) from recess 70l and is approximately 0.07" wide. This recess 70m has a bottom surface that can be arranged approximately 0.18" from a center axis of the opening 70i. As will be explained later on with regard to FIG. 15, the recesses 70j and 70k are sized and configured to receive projections 30g and 30h. This allows the inner sleeve 70 to slide over the holding member 30 when the lancet device is assembled. Then, the inner sleeve 70 can be rotated by approximately 45 degrees to the assembled position shown in, e.g., FIG. 1.

Opening 70*n* preferably tapers outwardly from surface 70*p* towards edge 70*b* at an angle of approximately 0.5 degrees (per side). The width of the rectangular inner surface 70*p* (measured up and down in FIG. 11E) may be approximately 0.40" while the width of the same surface (measured up and down in FIG. 1A) may be approximately 0.43". The walls 70*c*, 70*d*, 70*e* and 70*f* are configured to slide into opening 801 until shoulder 70*g* contacts edge 80*a* of back cap 80 and until projection 70*h* engages recess 80*m* of back cap 80. The projection 70*h* is a continuous projection and may have a radius of approximately 0.007" and may extend inwardly approximately 0.004". As was explained with regard to FIG. 10, this projection 70*h* is configured to fit into or otherwise engage with the continuous recess 80*m* of back cap 80 (see FIGS. 10C and 10D). Of course, the projection 70*h* need not be continuous, i.e., it does not have to extend continuously. It can instead be formed with intermitted projections or it may have the form of a single short projection on at least two opposite sides and that are centrally arranged with respect to walls 70*c*-70*f*. Of course, other connecting mechanisms, whether conventional or otherwise, may also be utilized in place of the projection and recess connection.

The side walls 70*c*-70*f* also preferably taper slightly from shoulder 70*g* to edge 70*b* by approximately 0.5 degrees (per side). The width of the rectangular edge at the bottom of the shoulder 70*g* (measured up and down in FIG. 1A) may be approximately 0.49" while the width of this edge (measured up and down in FIG. 11E) may be approximately 0.46". The distance between the shoulder 70*g* (measured across FIG. 11A) to surface 70*a* may be approximately 0.04". Side walls 70*c*, 70*d*, 70*e* and 70*f* also taper slightly from the bottom of surface 70*p* to edge 70*b*. The walls 70*c*-70*f* may also be curved outwards slightly (See FIG. 11D). In this regard, wall 70*c* may have a radius of approximately 0.95" (measured in the direction of FIG. 11D). Wall 70*d* may have a radius of approximately 0.9" (measured in the direction of FIG. 11D). Wall 70*e* may have a radius of approximately 0.43" (measured in the direction of FIG. 11D). Wall 70*f* may have a radius of approximately 0.43" (measured in the direction of FIG. 11D).

Figure 12A:
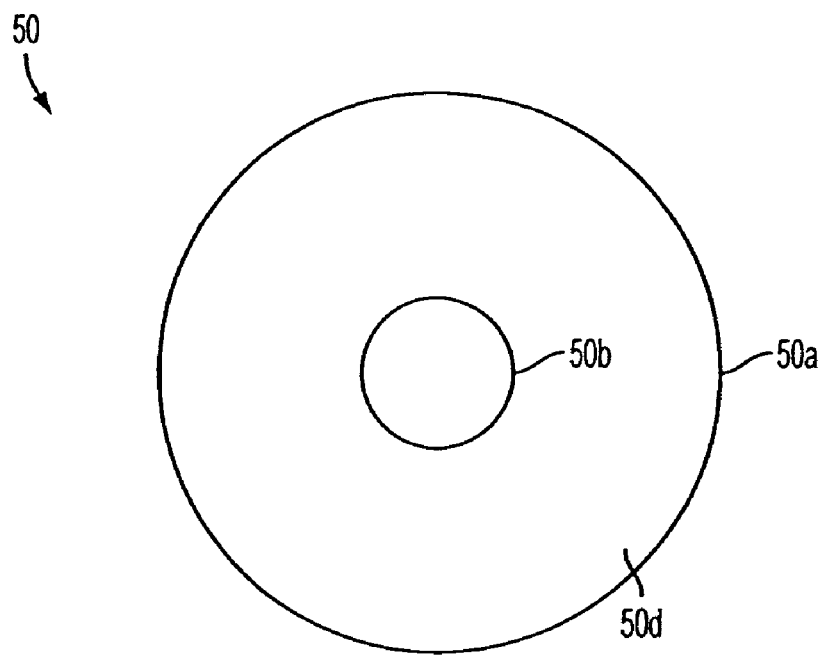
FIG. 12A shows a top view of the retaining member of the lancet device shown in FIG. 1.
Figure 12B:
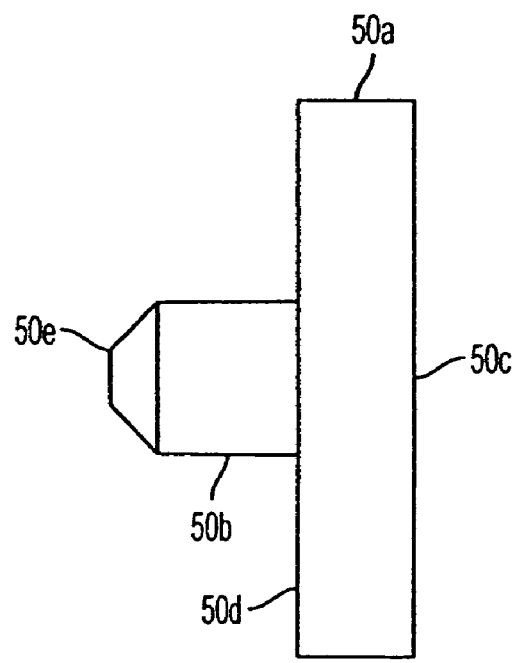
FIG. 12B shows a side view of the retaining member shown in FIG. 12A.

FIGS. 12A-B show top and side views of the retaining element 50. The retaining element 50 can preferably be made as one-piece structure by e.g., injection molding. In this regard, it is preferably made of a plastic or synthetic resin such as, e.g., ABS plastic. The retaining element 50 may also have be made of ABS—Light Blue and have a finish designated as SPI-C1. Additionally, the retaining element 50 may have an overall length that is approximately 0.13" (i.e., between edges 50*e* and 50*c*). Of course, other materials and/or finishes may be utilized, without leaving the scope of the invention. Moreover, the retaining element 50 may even be made of a plurality of sections of parts which are joined together to form the complete retaining element 50, without leaving the scope of the invention.

The retaining element 50 preferably has a front planar wall 50*d* and a rear planar wall 50*c*. A centrally disposed projection 50*b* extends from surface 50*d*. The projection 50*b* tapers inwardly from surface 50*d* to end 50*e*. The distance between end 50*e* to surface 50*d* can be approximately 0.8". The diameter of the projection 50*b* can be approximately 0.67" at surface 50*d* and can taper towards end 50*e* by approximately 11" (per side). The diameter of surface 50*a* can be approximately 0.25" and may similarly be tapered from side 50*c* to side 50*d* by approximately 1 degree (per side). End 50*e* can also have a chamfer that is approximately 0.02"×0.02".

Figure 13A:
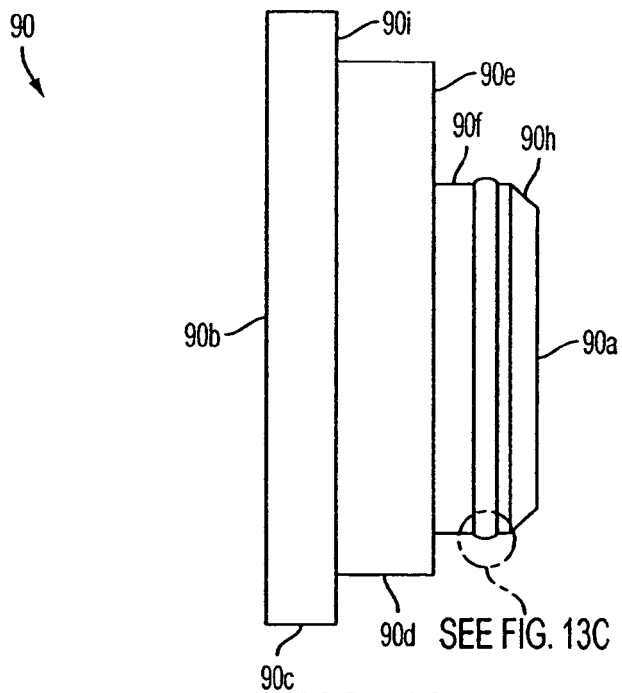
FIG. 13A shows a side view of the end plug of the lancet device shown in FIG. 1.
Figure 13B:
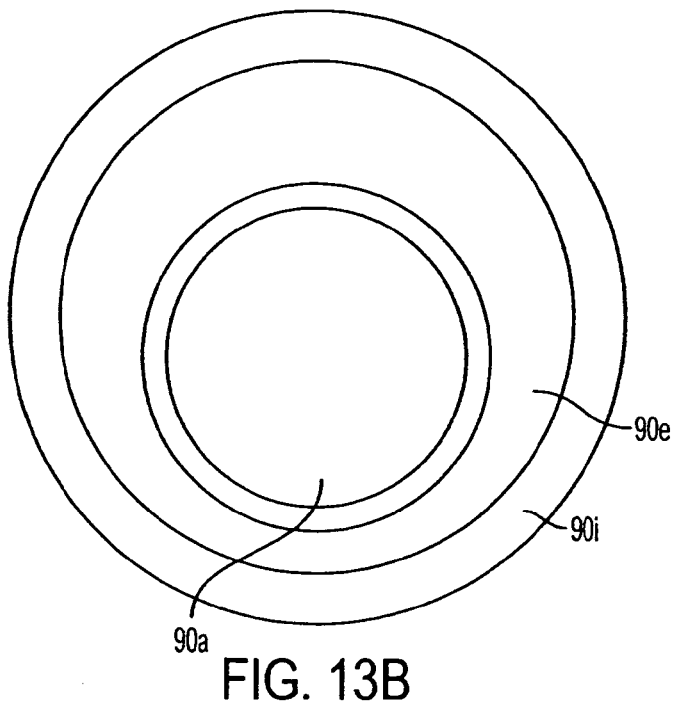
FIG. 13B shows a front end view of the end plug shown in FIG. 13A.
Figure 13C:
FIG. 13C shows an enlarged view of the circled portion shown in FIG. 13A.

FIGS. 13A-B show side and front views of the end plug 90. The end plug 90 can preferably be made as one-piece structure by e.g., injection molding. In this regard, it is preferably made of a plastic or synthetic resin such as, e.g., Delrin plastic. The end plug 90 may also have be made of Delrin—Natural and have a finish designated as SPI-C1. Additionally, the end plug 90 may have an overall length that is approximately 0.16" (i.e., between edges 90*b* and 90*a*). Of course, other materials and/or finishes may be utilized, without leaving the scope of the invention. Moreover, the end plug 90 may even be made of a plurality of sections of parts which are joined together to form the complete end plug 90, without leaving the scope of the invention.

The end plug 90 preferably has a rear planar wall 90*b* and a front planar wall 90*a*. A shoulder 90*i* is arranged between surfaces 90*b* and 90*e*. The diameter of cylindrical surface 90*c* can be approximately 0.37". The diameter of cylindrical surface 90*d* can be approximately 0.31". An offset projection 90*f* extends from surface 90*e* to end 90*a*. The distance between end 90*a* and surface 90*e* can be approximately 0.06". The distance between end 90*e* and surface 90*i* can be approximately 0.06". The distance between end 90*b* and surface 90*i* can be approximately 0.04". The diameter of the projection 90*f* can be approximately 0.21". The center of projection 90*f* can be offset from the center of diameter 90*c* by approximately 0.024". Projection 70*f* also includes a rounded continuous projection 90*g* which is sized to fit into a recess 30*k* of the holding member 30. The projection 90*g* may have a radius of 0.007" and may extend from surface 90*f* by approximately 0.004". End 90*a* can also have a chamfer that is approximately 0.015"×0.015".

Figure 14A:
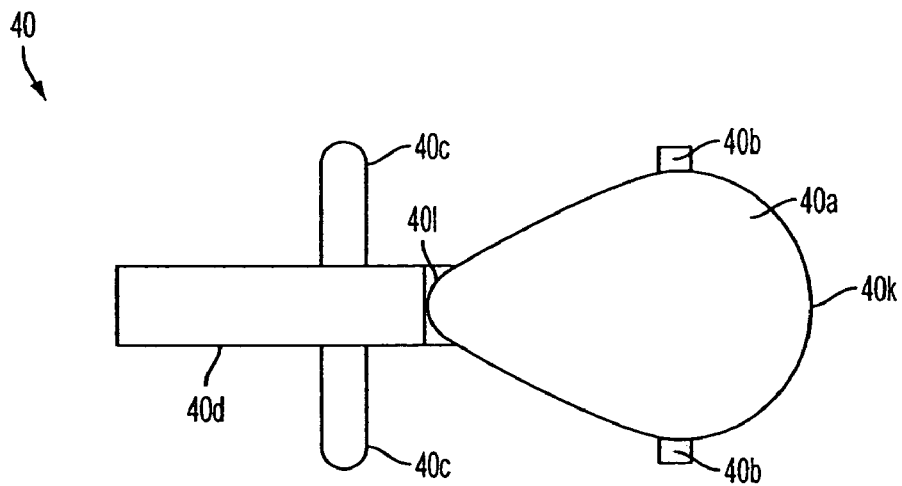
FIG. 14A shows a top view of the trigger element of the lancet device shown in FIG. 1.
Figure 14B:
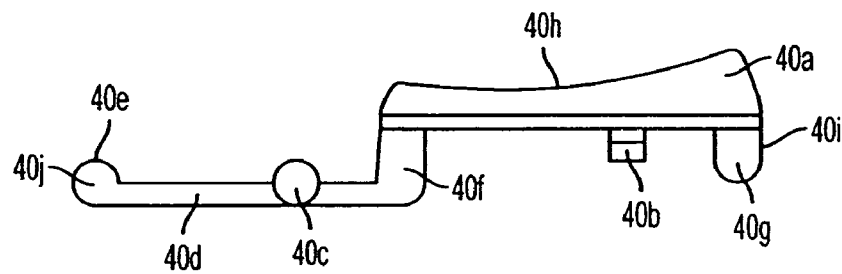
FIG. 14B shows a side view of the trigger element shown in FIG. 14A.
Figure 14C:
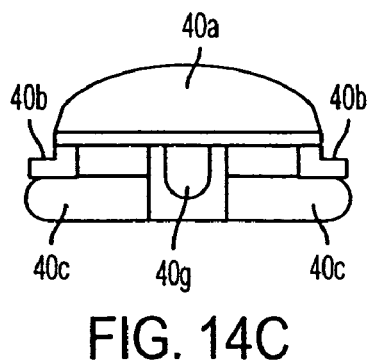
FIG. 14C shows a front view of the trigger element shown in FIG. 14B.
Figure 15A:
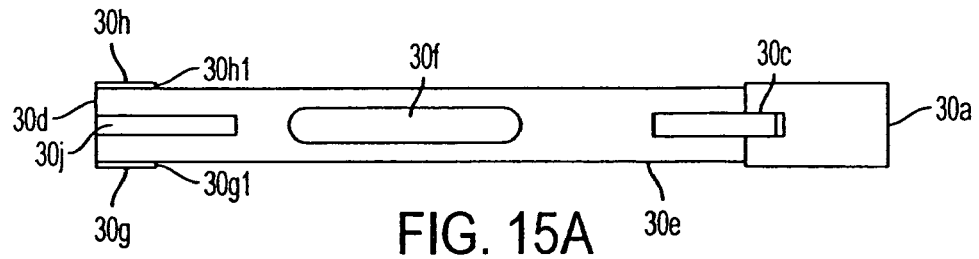
FIG. 15A shows a top view of the holding member of the lancet device shown in FIG. 1.
Figure 15B:
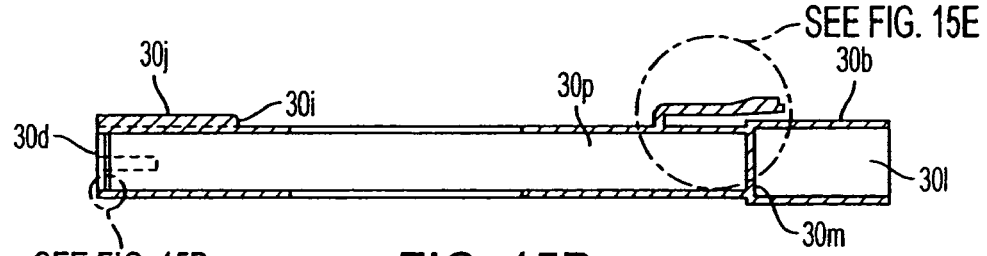
FIG. 15B shows a side cross-section view of the holding member shown in FIG. 15A.
Figure 15C:
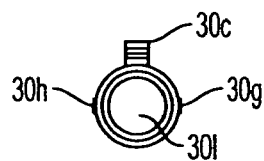
FIG. 15C shows a front view of the holding member shown in FIG. 15B.
Figure 15D:
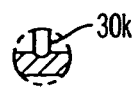
FIG. 15D shows an enlarged view of the small circled portion shown in FIG. 15B.
Figure 15E:
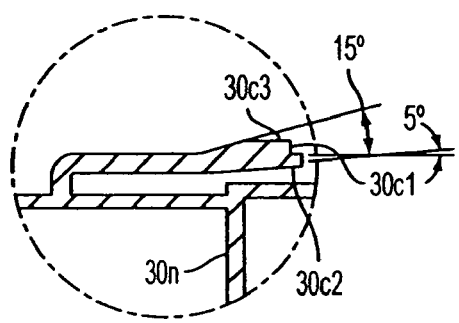
FIG. 15E shows an enlarged view of the large circled portion shown in FIG. 15B.

FIGS. 14A-C show top, side and front views of the trigger 40. The trigger 40 can preferably be made as one-piece structure by e.g., injection molding. In this regard, it is preferably made of a plastic or synthetic resin such as, e.g., ABS plastic. The trigger 40 may also have be made of ABS—Red and have a finish designated as SPI-A2. Additionally, the trigger 40 may have an overall length that is approximately 0.9" (i.e., between edges 40*j* and 40*i*). Of course, other materials and/or finishes may be utilized, without leaving the scope of the invention. Moreover, the trigger 40 may even be made of a plurality of sections of parts which are joined together to form the complete trigger 40, without leaving the scope of the invention.

The trigger 40 preferably has a end 40*j* that includes a rounded projection 40*e*. This rounded projection 40*e* is configured to contact an inner surface of upper body part 100 (see FIG. 1) and serves to brace or counter the movement of the trigger 40 when the trigger 40 is pressed into the lancet device. The projection 40*e* may have a radius of approximately 0.03". The trigger 40 also has end 40*i* that includes a rounded projection 40*g*. This rounded projection 40*g* is configured to contact surface 30*c*3 of deflecting member 30*c* of the holding member 30 (see FIG. 15) upon movement of the trigger 40, when the trigger 40 is pressed into the lancet device. The projection 40*g* may have a radius of approximately 0.03". The trigger 40 also includes a connecting member 40*f* which connects the push button 40*a* to the support 40*d*. Two shaft members or journals 40*c* project from opposite sides of the support 40*d*. The journals 40*c* may have a diameter of approximately 0.06" and may project approximately 0.16" from support 40*d*. These journals 40*c* also have rounded ends whose radius can be approximately 0.03". As explained previously, these journals 40*c* are configured to be mounted in the bearing supports formed by parts 100*j* and 110g. In this regard, the openings formed by these parts 100j and 110g should be sized to be the same or slightly larger than the diameter of journals 40c. In this way, the journals 40c can fit snugly in the supports 100j/110g. The width (measured in the direction of FIG. 14A) of the support 40d may be approximately 0.1".

The push button 40a preferably has a tear-drop shape and includes a inwardly curved (i.e., concave) surface 40h that has a radius of approximately 0.86". Two lip members 40b project from opposite sides of the push button 40a. These lip members are approximately 0.04" wide and may extend from the sides of the push button by approximately 0.03". The thickness of the lip members 40b (measured in the direction of FIG. 14C) can be approximately 0.02". These lip members 40b limit the upward movement of the push button 40a by contacting an inner surface of the upper body 100 when the trigger 40 is in the original non-deflected position (see e.g., FIG. 1). The push button 40a can have a curved front edge 40k whose radius can be approximately 0.17" and a curved rear edge 40l whose radius can be approximately 0.045". The distance between end 40j and right side surface of connecting element 40f can be approximately 0.42" while the distance between end 40i and right side surface of connecting element 40f can be approximately 0.4". Finally, the curved surface 40h can also include a texture (not shown) to prevent a user's finger from slipping off of the button 40a.

As explained above with regard to FIG. 1, the trigger 40 is designed to preferably deflect inwardly when a user pushes against the push button 40a (see FIG. 2) and to return to an original position (see FIG. 1 or 3). In this regard, the deflection occurs in the area between journals 40c and connecting element 40f and/or possibly somewhat between projection 40e and journals 40c. The design is such that the material properties of the trigger 40 allows it to act like a natural spring.

FIGS. 15A-E show top, side cross-section and front views of the holding member 30. The holding member 30 can preferably be made as one-piece structure by e.g., injection molding. In this regard, it is preferably made of a plastic or synthetic resin such as, e.g., Delrin plastic. The holding member 30 may also have be made of Delrin—Natural and have a finish designated as SPI-C1. Additionally, the holding member 30 may have an overall length that is approximately 2.8" (i.e., between edges 30a and 30d). Of course, other materials and/or finishes may be utilized, without leaving the scope of the invention. Moreover, the holding member 30 may even be made of a plurality of sections of parts which are joined together to form the complete holding member 30, without leaving the scope of the invention.

The holding member 30 preferably has a front end 30a that includes a cylindrical section 30b which may have a diameter of approximately 0.3". An opening 30l is arranged within the cylindrical section 30b. The opening 30l extends from a wall surface 30m to edge 30a. The diameter of the opening 30l at the edge 30a may be approximately 0.26" and may taper slightly, e.g., by approximately 0.5 degrees (per side), towards surface 30m. This tapered opening 30l is sized and configured to securely retain and receive the lancet 10 (see e.g., FIG. 1) which may be a conventional lancet. The holding member 30 also includes another cylindrical section 30e which may have a diameter of approximately 0.25". Cylindrical section 30e also has an internal opening 30p that extends from edge 30d to wall surface 30n. The opening 30p is sized and configured to receive springs S1 and S2 (see e.g., FIG. 1). The distance between surface 30n and edge 30d can be approximately 2.3". An elongated through slot 30f is arranged on the cylindrical section 30e. As discussed above, this slot 30f is sized and configured to receive projection 110h of the lower body part 110. In this regard, the width of the slot 30f can be approximately ⅛" while the length of the slot 30f can be approximately 0.825". The slot 30f also has rounded ends whose radius can be approximately ¹⁄₁₆".

A deflecting member 30c preferably extends from cylindrical section 30e. This deflecting member has a first stop surface 30c1 which is configured to abut shoulder 100i of the upper body part 100 and a second stop surface formed on a limit projection 30c2. A trigger engaging surface 30c3 is arranged an upper portion of the deflecting member 30c. This surface 30c3 is configured to be engaged by projection 40g of the trigger 40. As explained above, the deflecting member 30c is capable of deflecting inwards towards the holding member 30 when surface 30c3 is forced towards holding member 30. However, because the deflecting member 30c acts like a natural spring, the deflecting member 30c is capable of deflecting away from the holding member 30 when surface 30c3 is not being forced towards holding member 30. The length of the deflecting member 30c between surface 30c1 and where the member 30 extends from the wall 30e is approximately 0.43". In the area where the deflecting member 30c is coupled to the wall 30e, the deflecting member 30 is spaced from wall by about 0.08". The deflecting member 30 also has a width (measured in the direction of FIG. 15C) of approximately 0.08".

End 30d of the holding member 30 preferably includes three projections 30g, 30h and 30j. Projections 30g and 30h extend in the direction of the axis of the holding member 30 and are arranged opposite one another, i.e., 180 degrees apart. These projections 30g and 30h have a length of approximately 0.21" and a width of approximately 0.05". Projections 30g and 30h also have stop surfaces 30g1 and 30h1. These surfaces 30g1 and 30h1 are adapted to be engaged and/or contacted by surface 70p of the inner sleeve 70 when the back cap 80 is moved backwards to load the lancet device (see FIG. 5). Projection 30j includes a stop shoulder or surface 30i. As explained previously, the stop surface 30i engages and/or contacts the various cam surfaces 60e1-60e8 of the cam disk 60. Thus, the stop surface 30i serves to adjust the depth of the lancet needle based upon the position of the cam disk 60, as will be described later on. As explained previously, the projection 30j is configured to slide within the recess 70l of the inner sleeve 70 when the back cap 80 is moved from the positions shown in FIGS. 1 and 5.

Opening 30p, in the area of the end 30d, preferably includes a tapered portion that extends from edge 30d inwardly by approximately 0.5 degrees (per side). A continuous recess or indentation 30k is sized and configured to receive a projection 90g of the end plug 90. In this regard, the recess 30k may have a radius of approximately 0.007" and a depth of approximately 0.004". As can be seen in FIG. 1, diameter 90f of the end plug 90 is configured to slide into opening 30p of end 30d. Once the projection 90g engages recess 30k, the end plug 90 is secured to the holding member 30. As explained previously, surface 90a of the end plug 90 serves to engage or contact one end of spring S2. The end plug 90 is installed once springs S1 and S2 are arranged within the opening 30p, and after spring S3 is slid over end 30d.

FIGS. 16A-D show top, bottom and side cross-section views of the cam disk 60. The cam disk 60 can preferably be made as one-piece structure by e.g., injection molding. In this regard, it is preferably made of a plastic or synthetic resin such as, e.g., ABS plastic. The cam disk 60 may also have be made of ABS—Dark Blue and have a finish designated as MT-11040. Additionally, the cam disk 60 may have an overall diameter that is approximately 0.78". Of course, other materials and/or finishes may be utilized, without leaving the scope of the invention. Moreover, the cam disk 60 may even be made of a plurality of sections of parts which are joined together to form the complete cam disk 60, without leaving the scope of the invention.

Figure 16A:
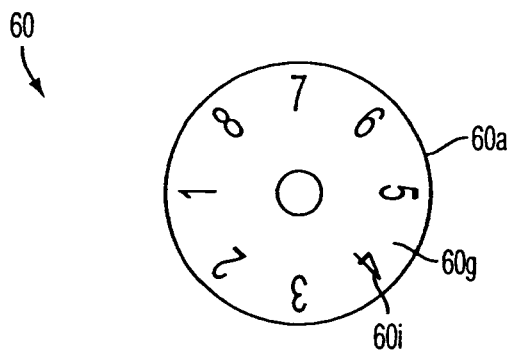
FIG. 16A shows a top view of the cam disk of the lancet device shown in FIG. 1.
Figure 16B:
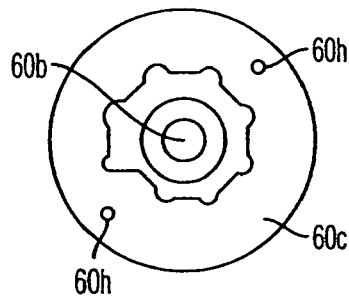
FIG. 16B shows a bottom view of the cam disk shown in FIG. 16A.
Figure 16C:
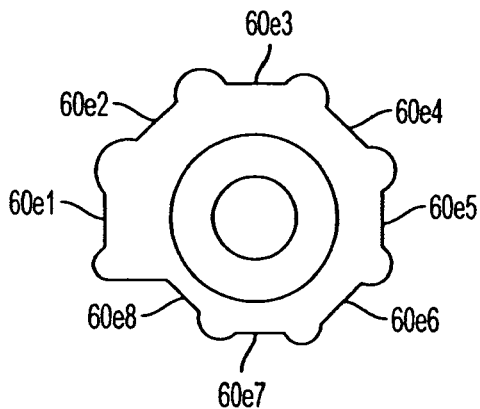
FIG. 16C shows an enlarged view of the cam portion of the cam disk shown in FIG. 16B.
Figure 16D:
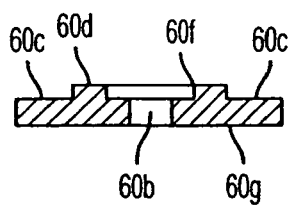
FIG. 16D shows a side cross-section view of the cam disk shown in FIG. 16B.

The cam disk 60 preferably has a top surface 60g that includes indicia 60i which may be numbers or letters. Of course, any desired indicia may be utilized. This indicia 60i can be, e.g., pad printed or silk screen raised numbers in white ink. The height of the indicia can be approximately 0.09". A centrally disposed opening 60b extends through the cam disk 60. The opening 60b may have a diameter of approximately ⅛". As explained previously, the opening 60b is sized and configured to slide over projection 1001 of the upper body part 100. The cam disk 60 also includes an enlarged diameter opening that is defined by shoulder 60f. The diameter of the shoulder can be approximately 0.25". The purpose of this shoulder 60f is to receive surface 50a of the retaining member 50 (see e.g., FIG. 1). The cam disk 60 includes a plurality of cam surfaces 60e1-60e8 formed on a cam section 60e. As can be seen in FIG. 16C, the cam surfaces 60e1-60e8 are all spaced from a center axis of the cam disk 60 by different amounts. As was explained previously, these surfaces are configured to be contacted by stop surface 30i of the holding member 30. Thus, for example, when contact is made between stop surface 30i and surface 60e1, the lancet needle will penetrate to its deepest setting. On the other hand, when contact is made between stop surface 30i and surface 60e8, the lancet needle will penetrate to its shallowest setting. Of course, surfaces 60e2-60e7 will set the penetrating depth in between these extreme settings. Although, the cam disk 60 is configured with eight settings (designated by the number of cam surfaces and the indicia), the cam disk 60 can have any number of desired settings that can range from two to as many as 20 or more, if desired.

In this regard, the distance between surface 60e8 and the center axis of cam disk 60 can be approximately 0.16", the distance between surface 60e7 and the axis of cam disk 60 can be approximately 0.169", the distance between surface 60e6 and the axis of cam disk 60 can be approximately 0.178" the distance between surface 60e5 and the axis of cam disk 60 can be approximately 0.187", the distance between surface 60e4 and the axis of cam disk 60 can be approximately 0.196", the distance between surface 60e3 and the axis of cam disk 60 can be approximately 0.205", the distance between surface 60e2 and the axis of cam disk 60 can be approximately 0.214", and the distance between surface 60e1 and the axis of cam disk 60 can be approximately 0.223". The surfaces 60e1-60e8 are separated by rounded projections which may have a radius of approximately 0.04". The width of the surfaces 60e1-60e8 can be approximately 0.08". The thickness of the cam section 60 can be approximately 0.05" measured from surface 60c and 60d while the thickness of the indicia section can be approximately 0.08" measured from surface 60g and surface 60c. Finally, the cam disk 60 preferably includes two indentations 60h which are sized and configured to receive rounded tips of the two projections 110j of the lower body part. These recesses can have depth of approximately 0.033" and a rounded bottom whose radius is approximately 0.02", and they may be spaced apart by approximately ⅝". The cam disk 60 may also include a knurl, a high-friction surface, or other desired texturing (e.g., projections and recesses) along its peripheral edge (not shown).

All the parts of the lancet device, with the exception of the springs S1-S3 (which can be made of spring steel) and with the exception of the lancet needle (which can be a conventional metal needle mounted to a conventional plastic lancet 10), may be made from plastic materials and can be formed using conventional injection molding techniques or other known manufacturing methods. The cam disk for example can be integrally formed with peripheral grooves and/or projections (similar to a coin), and with the indicating marks. However, when practical, other materials and manufacturing processes may also be utilized.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A lancet device, comprising:
   a body;
   a trigger mounted to the body;
   a front cover comprising a skin engaging end that includes a lancet opening through which a lancet needle extends;
   a holding member movably mounted within the body and comprising a front end and a rear end;
   the front end being configured to receive a lancet;
   a stop surface that moves with the holding member; and
   a cam disk comprising cam surfaces which can be contacted by the stop surface;
   the cam disk being configured to rotate at least partially,
   wherein the cam disk rotates about an axis that is not parallel to an axis running through at least one of the lancet opening and the holding member.

2. The lancet device of claim 1, further comprising a back cap configured to move between a retracted position and an original position.

3. The lancet device of claim 2, wherein the back cap is configured to move the holding member to a retracted position.

4. The lancet device of claim 2, wherein the back cap is coupled to a surface that engages the rear end of the holding member.

5. The lancet device of claim 2, wherein the back cap is coupled to an inner sleeve that includes a surface that engages the rear end of the holding member.

6. The lancet device of claim 5, wherein the inner sleeve comprises an opening that receives a rear end of the holding member.

7. The lancet device of claim 2, wherein the back cap is coupled to an inner sleeve that includes a surface that engages projections disposed on the rear end of the holding member.

8. The lancet device of claim 2, further comprising a spring for biasing the back cap towards an original position.

9. The lancet device of claim 1, further comprising a first spring for biasing the holding member towards an extended position and a second spring for biasing the holding member in an opposite direction.

10. The lancet device of claim 9, wherein the first and second springs are arranged within an axial opening of the holding member.

11. The lancet device of claim 9, wherein the first spring contacts zone side of a projection extending inwardly from the body and wherein the second spring contacts another side of the projection.

12. The lancet device of claim 11, wherein the projection extends into an elongated slot formed in the holding member.

13. The lancet device of claim 11, further comprising an end plug mounted to the rear end of the holding member.

14. The lancet device of claim 13, wherein the first spring is disposed between the projection and an inner wall surface arranged in the area of the front end of the holding member and wherein the second spring is disposed between the projection and the end plug.

15. The lancet device of claim 1, wherein the trigger is movably mounted to the body.

16. The lancet device of claim 1, wherein the front cover is removably mounted to the body.

17. The lancet device of claim 1, wherein the holding member comprises a projection that includes the stop surface.

18. The lancet device of claim 1, wherein the holding member comprises an integrally formed projection that includes the stop surface.

19. The lancet device of claim 1, wherein the front end comprises an opening that is configured to removably receive the lancet.

20. The lancet device of claim 1, further comprising a deflecting member configured to be deflected by the trigger.

21. The lancet device of claim 20, wherein the deflecting member is coupled to the holding member.

22. The lancet device of claim 20, wherein the deflecting member comprises a first stop surface that contacts a first surface of a holding projection extending inwardly from the body.

23. The lancet device of claim 22, wherein the deflecting member comprises a second stop surface that contacts a second surface of the holding projection.

24. The lancet device of claim 1, wherein the cam disk comprises indicia.

25. The lancet device of claim 24, wherein the cam surfaces are arranged on a cam section of the cam disk, the cam section being disposed on a side of the cam disk that is opposite a side that includes the indicia.

26. The lancet device of claim 1, wherein the cam disk comprises a centrally disposed opening that is mounted to a journal within the body.

27. The lancet device of claim 26, wherein the journal is coupled to the body.

28. The lancet device of claim 26, wherein the journal extends inwardly from the body.

29. The lancet device of claim 26, wherein the journal comprises a center axis that is generally perpendicular to the axis running through the molding member.

30. The lancet device of claim 1, wherein the cam disk rotates about an axis that is generally perpendicular to an axis running through at least one of the lancet opening and the holding member.

31. The lancet device of claim 1, wherein the cam disk is disposed between the trigger and a back cap.

32. The lancet device of claim 1, wherein the body comprises a two-piece body.

33. The lancet device of claim 32, wherein the cam disk is coupled to one of the two pieces of the two-piece body.

34. The lancet device of claim 33, wherein the front cover is removably mounted to the two-piece body.

35. The lancet device of claim 34, further comprising a back cap movably mounted to the two-piece body.

36. The lancet device of claim 1, wherein the body comprises at least one curved side indentation through which the cam disk protrudes.

37. The lancet device of claim 1, wherein the body comprises two oppositely arranged curved side indentations through which portions of the cam disk protrude.

38. The lancet device of claim 1, wherein the body comprises a mechanism for viewing indicia of the cam disk.

39. The lancet device of claim 1, wherein the mechanism for viewing indicia of the cam disk comprises an opening.

40. The lancet device of claim 1, further comprising a retaining element for one of axially retaining the cam disk and securing the cam disk to the body.

41. A method of using the lancet device of claim 1, the method comprising:
    rotating the cam disk to a desired set position;
    moving the holding member to a retracted position;
    maintaining the holding member in the retracted position until the trigger is triggered;
    disposing the skin engaging end of the lancet device against a user's skin; and
    triggering the trigger to cause movement of the holding member.

42. A method of puncturing a surface of skin using the lancet device of claim 1, the method comprising:
    adjusting a set depth of penetration of the needle by moving the cam disk to a desired set position;
    disposing the skin engaging end of the lancet device against a user's skin; and
    triggering the trigger to cause the lancet needle to penetrate the user's skin,
    wherein the puncture allows a blood sample to be taken.

43. A lancet device, comprising:
    a body;
    a trigger;
    a front cover comprising a skin engaging end that includes a lancet opening through which a lancet needle extends;
    a holding member movably mounted within the body and comprising a front end and a rear end;
    the front end being configured to receive a lancet;
    a stop projection coupled to the holding member; and
    a cam disk comprising indicia and cam surfaces which can be contacted by the stop projection;
    the cam disk being configured to rotate at least partially,
    wherein the cam disk is mounted to a projection that extends inwardly from the body.

44. A lancet device, comprising:
    a body;
    a trigger;
    a front cover comprising a skin engaging end that includes a lancet opening through which a lancet needle extends;
    a holding member movably mounted within the body and comprising a front end and a rear end;
    the front end being configured to receive a lancet;
    a back cap configured to move the holding member to a retracted position;
    a stop surface coupled to the holding member;
    a cam disk at least partially arranged within the body;
    the cam disk comprising indicia and cam surfaces which can be contacted by the stop projection; and
    the cam disk being configured to rotate at least partially about an axis that is not parallel to an axis running through the holding member,
    wherein the cam disk protrudes from at least one side wall of the body.

45. A lancet device, comprising:
a body;
a trigger;
a front cover comprising a skin engaging end that includes a lancet opening through which a lancet needle extends;
a holding member movably mounted within the body and comprising a front end and a rear end;
the front end being configured to receive a lancet;
a back cap configured to move the holding member to a retracted position;
a stop surface that moves with the holding member;
a cam mechanism at least partially arranged within the body;
the cam mechanism comprising at least one peripheral cam surface which can be contacted by the stop surface; and
the cam mechanism being configured to rotate at least partially about an axis that is perpendicular to an axis running through the holding member,
wherein the cam mechanism adjusts a depth penetration based upon a rotational position of the at least one peripheral cam surface.

46. The lancet device of claim 45, wherein the at least one peripheral cam surface comprises a plurality of peripheral cam surfaces arranged at different distances relative to a rotational axis of the cam mechanism.

47. The lancet device of claim 46, wherein the plurality of peripheral cam surface comprise curved peripheral surfaces.

48. The lancet device of claim 45, wherein the at least one peripheral cam surface is arranged parallel to a rotational axis of the cam mechanism.

49. A method of puncturing a surface of skin using the lancet device of claim 45, the method comprising:
adjusting a set depth of penetration of the needle by moving the cam mechanism to a desired set position;
disposing the skin engaging end of the lancet device against a user's skin; and triggering the trigger to cause the lancet needle to penetrate the user's skin,
wherein the puncture allows a blood sample to be taken.

50. A method of using the lancet device of claim 45, the method comprising:
rotating the cam mechanism to a desired set position;
moving the holding member to a retracted position;
maintaining the holding member in the retracted position until the trigger is triggered;
disposing the skin engaging end of the lancet device against a user's skin; and
triggering the trigger to cause movement of the holding member.

51. A lancet device, comprising:
a body comprising a skin engaging end that includes a lancet opening through which a lancet needle extends;
a holding member movably mounted within the body and comprising the lancet needle;
a stop surface that moves with the holding member;
a cam mechanism rotatably mounted within the body;
a portion of the cam mechanism projecting from at least one side opening of the body;
the cam mechanism comprising at least one cam surface which can be contacted by the stop surface; and
the cam mechanism being configured to rotate at least partially about an axis that is not parallel to an axis running through the holding member,
wherein the cam mechanism adjusts a depth penetration of the lancet needle based upon a rotational position of the cam mechanism.

52. The lancet device of claim 51, further comprising a back cap configured to move between a retracted position and an original position.

53. The lancet device of claim 52, wherein the back cap is configured to move the holding member to a retracted position.

54. The lancet device of claim 52, wherein the back cap is coupled to a surface that engages the rear end of the holding member.

55. The lancet device of claim 52, further comprising a spring for biasing the back cap towards an original position.

56. The lancet device of claim 51, further comprising a spring for biasing the holding member towards an extended position.

57. The lancet device of claim 51, further comprising a first spring for biasing the holding member towards an extended position and a second spring for biasing the holding member in an opposite direction.

58. The lancet device of claim 51, further comprising a trigger movably mounted to the body.

59. The lancet device of claim 58, further comprising a deflecting member configured to be deflected by the trigger.

60. The lancet device of claim 59, wherein the deflecting member is coupled to the holding member.

61. The lancet device of claim 51, wherein the holding member comprises a projection that includes the stop surface.

62. The lancet device of claim 51, wherein the holding member comprises an integrally formed projection that includes the stop surface.

63. The lancet device of claim 51, wherein the cam mechanism comprises a cam disk that includes indicia.

64. The lancet device of claim 63, wherein the at least one cam surface is arranged on a cam section of the cam disk, the cam section being disposed on a side of the cam disk that is opposite a side that includes the indicia.

65. The lancet device of claim 51, wherein the cam mechanism comprises a centrally disposed opening that is mounted to a journal within the body.

66. The lancet device of claim 65, wherein the journal comprises a center axis that is generally perpendicular to the axis running through the holding member.

67. The lancet device of claim 51, wherein the cam mechanism rotates about an axis that is generally perpendicular to an axis running through at least one of the lancet opening and the holding member.

68. The lancet device of claim 51, wherein the body comprises a two-piece body.

69. The lancet device of claim 51, wherein the body comprises at least one curved side indentation through which the portion of the cam mechanism protrudes.

70. The lancet device of claim 51, wherein the body comprises two oppositely arranged curved side indentations through which the portion and another portion of the cam mechanism protrude.

71. The lancet device of claim 51, wherein the body comprises a mechanism for viewing indicia of the cam mechanism.

72. The lancet device of claim 71, wherein the mechanism for viewing indicia of the cam mechanism comprises an opening.

73. The lancet device of claim 51, wherein the cam mechanism comprises a circular cam disk.

74. A method of using the lancet device of claim 51, the method comprising:
rotating the cam mechanism to a desired set position;
maintaining the holding member in a retracted position until a trigger is triggered;
disposing the skin engaging end against a user's skin; and
triggering the trigger to cause movement of the holding member.

* * * * *

UNITED STATES PATENT AND TRADEMARK OFFICE
CERTIFICATE OF CORRECTION

PATENT NO. : 7,621,931 B2 Page 1 of 1
APPLICATION NO. : 10/441065
DATED : November 24, 2009
INVENTOR(S) : Steven Schraga It is certified that error appears in the above-identified patent and that said Letters Patent is hereby corrected as shown below:

On the Title Page under Inventor name, change "Shraga" to --Schraga--.

At column 24, line 30 (claim 42, line 7) of the printed patent, "penetrate" should be --puncture--.

At column 25, line 37 (claim 49, line 7) of the printed patent, "penetrate" should be --puncture--.

Signed and Sealed this

Sixth Day of July, 2010

David J. Kappos
*Director of the United States Patent and Trademark Office*